United States Patent
Quigley et al.

(10) Patent No.: US 7,589,173 B2
(45) Date of Patent: Sep. 15, 2009

(54) METHODS FOR DIAGNOSING CANCER AND DECREASING METASTASIS BY CANCER CELLS

(75) Inventors: James P. Quigley, La Jolla, CA (US); John D. Hooper, Mitchelton (AU); Jacqueline E. Testa, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 107 days.

(21) Appl. No.: 10/781,564

(22) Filed: Feb. 18, 2004

(65) Prior Publication Data

US 2004/0247601 A1   Dec. 9, 2004

Related U.S. Application Data

(60) Provisional application No. 60/448,828, filed on Feb. 19, 2003.

(51) Int. Cl.
*C07K 14/00* (2006.01)

(52) U.S. Cl. ..................................................... 530/350

(58) Field of Classification Search ........................ None
See application file for complete search history.

(56) References Cited

U.S. PATENT DOCUMENTS

| 6,245,898 | B1 | 6/2001 | Testa et al. | |
|---|---|---|---|---|
| 6,498,014 | B1 | 12/2002 | Testa et al. | |
| 2002/0142003 | A1* | 10/2002 | Schweifer et al. | 424/185.1 |

FOREIGN PATENT DOCUMENTS

| WO | WO-99/66027 A1 | 12/1999 |
|---|---|---|
| WO | WO-02/04508 A1 | 1/2002 |
| WO | WO 02070539 A2 * | 9/2002 |
| WO | WO02070539 A2 * | 9/2002 |

OTHER PUBLICATIONS

Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in "The Protein Folding Problem and Tediary Structure Prediction", 1994, Merz, et al. (ed.), Birkhauser, Boston, MA, pp. 433, and 492-495.*
Accession No. Q9H5V8 information sheet and revision history, total pages 3.*
"International Search Report for corresponding PCT Application No. PCT/EP2004/001556", (Jun. 3, 2004), 5 pgs.
Brooks, P. C., "Subtractive Immunization Yields Monoclonal Antibodies That Specifically Inhibit Metastasis", *Journal of Cellular Biology*, 122(6), (1993), 1351-1359.
Hooper, J. D., et al., "*Homo sapiens* NCSG135 mRNA, Complete cds", *Database EMBL Online, Retrieved From EBI*, Database Accession No. AF468010, Feb. 2, 2003), 3 pgs.
Hooper, J. D., et al., "Subtractive Immunization Using Highly Metastatic Human Tumor Cells Identifies SIMA135/CDCP1, A 135 kDa Cell Surface Phosphorylated Glycoprotein Antigen", *Oncogene*, 22(12), (2003), 1783-1794.
Komatsoulis, G., et al., "Sequence 132 From Patent US 6,476,195", *Database NCBI Online, Retrieved from EBI*, Database Accession No. AAN97616, (Dec. 20, 2002), 1 pg.
Scherl-Mostageer, Marwa, et al., "Identification of a Novel Gene, CDCP1, Overexpressed in Human Colorectal Cancer", *Oncogene*, 20(32), (2001), 4402-4408.
Sugano, S., et al., "*Homo sapiens* cDNA: FLJ22969 fis. Clone KAT10759", *Database EMBL Online, Retrieved From EBI*, Database Accession No. AK026622, (Sep. 29, 2000), 3 pgs.
Testa, J. E., et al., "Eukaryotic Expression Cloning With an Antimetastatic Monoclonal Antibody Identifies a Tetraspanin (PETA-3/CD151) as an Effector of Human Tumor Cell Migration and Metastasis", *Cancer Research*, 59(15), (1999), 3812-3820.
Zijlstra, A., et al., "Targeting the Proteome/Epitome, Implementation of Subtractive Immunization", *Biochemical and Biophysical Research Communications*, 303(3), (2003), 733-744.
Abe, K., "Rapid isolation of desired sequences from lone linker PCR amplified cDNA mixtures: application to identification and recovery of expressed sequences in cloned genomic DNA.", *Mamm Genome*, 2(4), (1992),252-9.
Sugano, S., et al., "NEDO human cDNA sequencing project-BAB15511 unnamed protein", *Direct submission; NCBI Sequence Viewer*, www.ncbi.nlm.nih.gov/entrez/viewer.fcgi?db=protein&id=10439515 (1 of 2) Jul. 3, 2007 4:19:09 PM, (Submitted Aug. 29, 2000), 2 pages.

* cited by examiner

*Primary Examiner*—Christopher H Yaen
*Assistant Examiner*—Hong Sang
(74) *Attorney, Agent, or Firm*—Schwegman, Lundberg & Woessner, P.A.

(57) ABSTRACT

The invention provides a protein that is a tumor marker protein. This protein can be used to prepare antibodies that bind to the tumor marker protein. These antibodies can be used to reduce, or eliminate metastasis by cancer cells that produce the tumor marker protein. In addition, the invention provides methods that can be used to diagnose cancer, and metastasis by cancer cells.

3 Claims, 15 Drawing Sheets

FIG. 2B (SEQ ID NO:1)

METHODS FOR DIAGNOSING CANCER AND DECREASING METASTASIS BY CANCER CELLS

REFERENCE TO RELATED APPLICATION

The present application claims priority under 35 U.S.C. 119(e) to U.S. Provisional Patent Application No. 60/448,828 filed Feb. 19, 2003, which is hereby incorporated by reference.

GOVERNMENT FUNDING

The invention described herein was developed with support from the National Institutes of Health under Grant Numbers CA65660, HL31950, and Training Grants T32 HL07695 and T32 HL07195. The U.S. Government may have certain rights in the invention.

FIELD OF THE INVENTION

The invention relates generally to methods to diagnose cancer and to decrease metastasis by cancer cells in a mammal, such as a human. More specifically, the invention relates to the use of a tumor marker protein to create antibodies that can be used to detect increased production of the protein in a cell, and use of the antibodies to decrease metastasis by cancer cells that produce the tumor marker protein.

BACKGROUND OF THE INVENTION

A malignant tumor sheds cells which migrate to new tissues and create secondary tumors while a benign tumor does not generate secondary tumors. The process of generating secondary tumors is called metastasis and is a complex process in which tumor cells colonize sites distant from the primary tumor. Tumor metastasis remains the major cause of deaths in cancer patients, yet the molecular mechanisms underlying tumor cell dissemination are not clearly understood.

Metastasis is a multi-step process in which tumor cells must detach from the primary tumor, invade the cellular matrix, penetrate through blood vessels, thus enter the circulatory system (intravasate), arrest at a distant site, exit the blood stream (extravasate), and grow. See, e.g., G. L. Nicolson (1982) Biochim. Biophis. Acta. 695: 113-176; G. L. Nicolson and G. Poste (1983) In. Rev. Exp. Pathol. 25: 77-181; G. Poste and I. J. Fidler (1980) Nature 283: 139-145; and E. Roos (1984) Biochim. Biophis. Acta. 738: 263-284. Given the complexity of the process, it is thought that numerous genes mediate tumor cell metastasis. Indeed, the metastatic phenotype has been correlated with expression of a variety of proteins, including proteases, adhesion molecules, and the like. However, evidence that a given protein is directly involved in dissemination is often lacking, or difficult to prove. L. A. Liotta and W. Stetler-Stevenson (1989) J. Natl. Cancer Inst. 81: 556-557.

The human epidermoid carcinoma, HEp-3, provides a unique system that can be used to detect and characterize genes which effect metastatic dissemination. HEp-3 cells, propagated by serial passage on the chick chorioallantoic membrane (CAM), are both tumorigenic and spontaneously metastatic (T+M+). L. Ossowski and E. Reich (1980a) Cancer Res. 40: 2300-2309. However, when such cells are grown continuously in vitro, they readily form primary tumors, but progressively become non-metastatic (T+M−) with time. L. Ossowski and E. Reich (1980b) Cancer Res. 40: 2310-2315. With prolonged cultivation in vitro, they eventually become non-tumorigenic also (T−M−). The loss of metastatic ability is reversible. T+M− cells carried on the chorioallantoic membrane for two to three passages regain the ability to form spontaneous metastases. Thus, by altering growth conditions, the metastatic potential of these cells can be manipulated by the investigator.

Human urokinase-type plasminogen activator (uPA) was shown to be directly involved in dissemination of HEp-3, as spontaneous metastasis of HEp-3 cells in the chick embryo was inhibited by antibodies that were specific for human uPA. L. Ossowski and E. Reich (1983b) Cell 35: 611-619. Subsequently, it was observed that inhibition of uPA activity blocked infiltration of the CAM mesenchyme by individual HEp-3 cells. L. Ossowski (1988a) Cell 52: 321-328. However, active uPA appeared to be required for tumor cell intravasation but not extravasation. L. Ossowski (1988a). Thus, some other factor(s) must be also involved in HEp-3 dissemination and in dissemination of cancer cells in general. J. P. Quigley et al. (1988) Ciba Foundation Symposium 141: 22-47, Brooks et al. (1993) J. Cell Biol. 122 (6): 1351-1359 and Testa, et al. in U.S. Pat. Nos. 6,245,898 and 6,498,014 describe the generation of monoclonal antibodies (mAbs), using "subtractive immunization", which recognize cell surface antigens expressed on HEp-3 cells and inhibit tumor metastasis in the chorioallantoic membrane model. Nevertheless, these antigens have not been correlated to in vivo metastasis nor shown to be directly involved in the process of in vivo metastasis.

Consequently, there is a need to identify biological molecules that are functionally involved in cancer cell dissemination in order to develop therapies that can be used to inhibit the migration of tumor cells to new tissues. Also, methods to inhibit tumor cell metastasis and to diagnose cancer are needed to help in the battle to control cancer by reducing or eliminating the spread of cancer cells throughout the body of a mammal afflicted with cancer.

SUMMARY OF THE INVENTION

The present invention concerns the identification and characterization of a protein (SIMA135) (SEQ ID NO:1) that is produced in metastatic cells. Accordingly, the invention provides SIMA135 in glycosylated and non-glycosylated form. The invention also provides antibodies that specifically and selectively bind to SIMA135, and fragments of SIMA135. These antibodies can bind to SIMA135, or fragments of SIMA135, that are glycosylated or non-glycosylated. Accordingly, the invention provides methods to prevent, reduce, or eliminate metastasis of cancer cells through use of antibodies that specifically bind to SIMA135. The invention also provides methods to diagnose cancer, and to determine the presence of cancer cells in a test sample. These methods may be used in association with a mammal, such as a human. The invention also provides pharmaceutical compositions and kits that contain antibodies that specifically and selectively bind to SIMA135 and fragments of SIMA135. The invention also provides a method to screen for agents that modulate production of SIMA135 by a cell.

The invention provides SIMA135, and fragments of SIMA135. Preferably SIMA135 or a fragment of SIMA135 is not glycosylated. More preferably the SIMA135 or the fragment of SIMA135 is glycosylated. Preferably fragments of SIMA135 are antigenic and are able to elicit an immune response when administered to an organism, such as a mammal or an avian. Preferably the antigenic fragments of SIMA135 are glycosylated.

The invention provides antibodies that bind to SIMA135 or fragments of SIMA135 such as monoclonal antibody 41-2. Preferably, the antibody is not monoclonal antibody 41-2 as the monoclonal antibody preferably selectively and specifically binds with SIMA135. Preferably the antibodies are recombinant antibodies. More preferably the antibodies are polyclonal antibodies. Even more preferably the antibodies are humanized antibodies. Most preferably the antibodies are monoclonal antibodies. Preferably the antibodies bind to non-glycosylated SIMA135 or to a non-glycosylated fragment of SIMA135. More preferably the antibodies bind to glycosylated SIMA135, or a glycosylated fragment of SIMA135.

The invention provides a method to prevent, reduce, or eliminate metastasis of a cancer cell. The method involved administering an antibody that binds to SIMA135 to an organism in need thereof. Monoclonal antibody 41-2 can bind SIMA135 and also with other antigens involved in metastasis but it is preferred that the antibody of the method should be other than monoclonal antibody 41-2. Such other antibody will selectively and specifically bind with SIMA135. Preferably the organism is a mammal. More preferably the organism is a human. Preferably the antibody binds to SIMA135, or to a fragment thereof, non-specifically. More preferably the antibody binds to SIMA135, or a fragment thereof, specifically. Preferably the antibody is a polyclonal antibody. More preferably the antibody is a recombinant antibody. Even more preferably the antibody is a monoclonal antibody. Most preferably the antibody is a humanized antibody. Preferably the antibodies bind to non-glycosylated SIMA135 or to a non-glycosylated fragment of SIMA135. More preferably the antibodies bind to glycosylated SIMA135, or a glycosylated fragment of SIMA135. Preferably the antibody is administered to the organism is need thereof in as a pharmaceutical composition.

The invention also provides methods to diagnose cancer in an organism. In one embodiment, antibodies that bind to SIMA135 can be contacted with a test sample obtained from the organism, and then the relative amount of antibodies that bind to the test sample are compared to the relative amount of antibodies that bind to a non-cancerous control sample. Increased antibody binding to the test sample relative to the control sample indicates that the organism has cancer. In another embodiment, the invention provides an immunohistochemical method to diagnose cancer in an organism wherein antibodies are contacted with a test sample obtained from the organism, and the antibody binding pattern exhibited by the test sample is compared to an antibody binding pattern produced through use of a control sample. If the antibody binding pattern produced using the test sample matches an antibody pattern produced through use of a cancerous control sample, the organism is diagnosed as having cancer. Alternatively, if the antibody binding pattern to the test sample is different than an antibody binding pattern produced through use of a non-cancerous control sample, then the organism is diagnosed as having cancer. Preferably the antibody binds non-specifically to SIMA135, or a fragment thereof. More preferably the antibody binds specifically to SIMA135, or a fragment thereof.

The invention also provides pharmaceutical compositions that contain an antibody that binds to SIMA135, or a fragment thereof, and a pharmaceutical carrier provided that the antibody is not monoclonal antibody 41-2.

The invention also provides kits that contain an antibody that binds to SIMA135, or a fragment of SIMA135, and packaging material.

The invention provides a method to identify agents that modulate production of SIMA135 by a cell. The invention as well includes the cell line operable in the method as well as the assay method itself. Preferably an agent identified according to the method increases production of SIMA135 by a cell. Such an identification will demonstrate carcinogenicity of such an agent and thus can be used as a rapid test for cancer-causing agents. More preferably an agent identified according to the method decreases production of SIMA135 by a cell. Such an identification will demonstrate the anti-carcinogenicity of such an agent. In one embodiment, a candidate agent is contacted with a test cell and production of SIMA135 by the test cell is compared to a control cell that was not contacted with the candidate agent. An increase or decrease in SIMA135 production by the test cell as compared to the control cell indicates that the candidate agent modulates production of SIMA135 by a cell. Preferably the cell is a mammalian cell. More preferably the cell is a human cell. Even more preferably the cell is a non-metastatic HEp3 cell. Most preferably the cell is a metastatic HEp3 cell.

BRIEF DESCRIPTION OF THE DRAWINGS

FIG. 1 shows that monoclonal antibody 41-2, generated by subtractive immunization, recognizes a 135 kDa protein that is more highly expressed by metastatic HEp3 cells.

FIG. 2 illustrates the identification of the 135 kDa antigen, SIMA135, recognized by mAb 41-2. FIG. 2(B) illustrates the amino acid sequence of SIMA135 (SEQ ID NO:1). The signal sequence is in lower case lettering and the putative transmembrane domain is boxed. Twelve consensus N-glycosylation motifs are indicated with filled triangles. Cytoplasmic tyrosine residues are circled. CUB domains that are thought to span residues 221 to 348 and 417 to 544 are underlined. The three peptides identified from trypsin digestion and sequencing are overlined. The Arg residue preceding peptide 2 and the Lys preceding peptide 3 are boxed to highlight the consistency with trypsin specificity for Arg/Lys containing substrates. Cytoplasmic domain PXXP sequences are underlined. A consensus palmitylation motif, following the putative transmembrane domain, is indicated by filled circles.

FIG. 3 illustrates expression of SIMA135 in tissues and cells.

FIG. 5 shows the characterization of SIMA135.

FIG. 6 shows immunohistochemical analysis of SIMA135 expression in normal and cancerous colon. Sections (6 μm) were stained with mAb 41-2 as primary antibody.

FIG. 8 is a Western blot of lysates prepared from the 7 different cell lines probed with MoAb41-2. Two exposures of the blot are presented.

DETAILED DESCRIPTION OF THE INVENTION

Figure 1A:
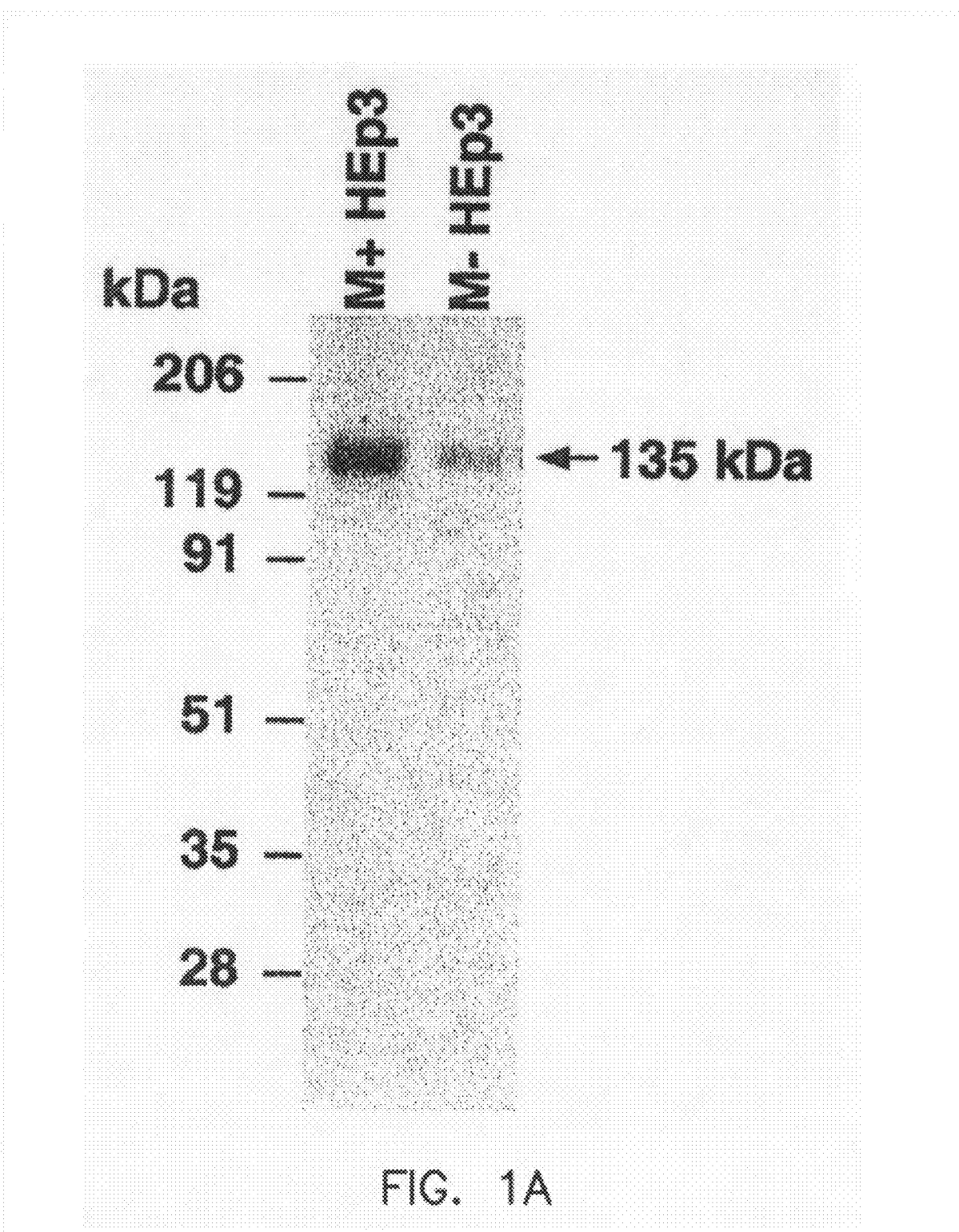
FIG. 1(A) shows western blot analysis, using mAb 41-2, of lysates (20 μg) prepared from high metastatic ($M^+$) and low metastatic ($M^-$) HEp3 cells electrophoresed under non-reducing conditions.

The invention relates to the discovery of a glycosylated protein that was purified from metastatic HEp3 cells through subtractive immunization using a monoclonal antibody designated 41-2. The protein is designated SIMA135 (subtractive immunization M$^+$ HEp3 associated 135 kDa protein).

SIMA135 refers to a protein that can be physically isolated from cells, as opposed to being a punitive protein predicted from translation of a nucleic acid sequence. Physical isolation of the SIMA135 protein is significant for a number of reasons. One reason is that isolation of the protein indicates that the mRNA is actually translated into a polypeptide. Secondly, isolation and characterization of the protein as reported herein indicates that the protein is glycosylated. Physical isolation of the glycosylated protein confirms that glycosylation sites within the polypeptide are available for glycosylation and are not buried within the folded protein to become inaccessible to glycosyltransferases. Such conformation is important due to the known role that glycosylation plays in protein folding and immunogenicity. Therefore, isolation of the SIMA135 protein is a significant advance when compared to a theoretical polypeptide sequence predicted from a nucleic acid sequence.

The SIMA135 cDNA is shown herein to encode a 135 kDa type I transmembrane cell surface protein that specifically immunoreacts with mAb 41-2. Immunopurification and amino acid sequencing confirms that the mature protein commences at Phe30 following removal of a 29 amino acid signal peptide. Immunocytochemical analysis confirms localization of the protein to the cell surface and the type I orientation of this protein. In addition, consistent with the presence of 12 potential extracellular glycosylation sites, Western blot analysis of deglycosylated cell lysates indicates that up to 40 kDa of the difference between the apparent (~135 kDa) and theoretical (~90 kDa) molecular weight of mature SIMA135 is due to N-linked glycans. Western blot analysis demonstrates that SIMA135 is a phosphotyrosine protein, consistent with the presence of 5 intracellular tyrosine residues. In addition, the inhibitor PP2 has been used to demonstrate that a Src kinase family member acts to phosphorylate tyrosines of SIMA135 in HEp3 cells.

The domain structure of SIMA135 indicates that it may interact with extracellular proteins such as soluble ligands, other cell surface proteins and/or matrix components; potentially via putative CUB domains present within its amino terminal region. These structures are thought to mediate binding to a variety of protein ligands. For example, homodimerization of the MASP serine proteases acting within the lectin branch of the complement cascade is stabilized through interactions involving CUB domains (Chen and Wallis, 2001). Also a number of the type II transmembrane serine proteases contain CUB domains thought to mediate enzyme-substrate interactions (Hooper et al., 2001). In addition, CUB domains of cubilin mediate binding to both the intrinsic factor-cobalamin as well as albumin (Yammani et al., 2001). As SIMA135 is heavily glycosylated within its extracellular domain, it is thought that ligand binding will be, at least partially, dependent on carbohydrate moieties as has been demonstrated for various isoforms of the cell surface glycoprotein CD44 (Bajorath, 2000). Glycosylation is also thought to contribute to SIMA135 protein folding, and trafficking to and maintenance at the cell surface (Gorelik et al., 2001; Grogan et al., 2002).

SIMA135 displayed differences in amino acid sequence from other proteins associated with signet ring carcinoma (GenBank entry AK026622) and the non small lung cell carcinoma cell line Calu 6 (GenBank entry AY026461) (Scherl-Mostageer et al., 2001). These differences are thought to affect the ability of SIMA135 to interact with other molecules, as compared to previously known proteins. The first amino acid change, 525Arg→Gln, occurs within an extracellular potential ligand binding domain; the second of the potential CUB domains of SIMA135. The second amino acid change, 709Gly→Asp, is located 2 residues after a tyrosine residue. This change from a non-polar amino acid to a charged residue could be expected to have a significant impact on the ability of the proximal tyrosine to be phosphorylated, and therefore is thought to have an impact on the capacity of SIMA135 to bind to, for example, SH2 domains. The last change, 827Ser→Asn, is located 4 residues from a PXXP motif. Accordingly, this change may also impact on the ability of SIMA135 to interact with other proteins; in this case SH3 domain containing proteins.

In normal colon tissue, SIMA135 protein is observed on basal and apical surfaces of epithelial cells lining the colon lumen and on the apical surface of crypt epithelial cells. In contrast to its distinct localization in normal colon, SIMA135 distribution in colon tumor tissue is disarrayed and heterogeneous, appearing dysregulated with both plasma membrane and cytoplasmic staining. It appears that expression of SIMA135 is more intense in invading glands deeper in the colonic serosa and within draining blood vessels. These results indicate that increased SIMA135 protein expression is associated more with later stages of carcinogenesis, such as local invasion and metastasis. This proposal is partly supported by Western blot analysis of pairs of human tumor cell lines originating from the same tissue. For example, SIMA-135 levels were much higher in highly-metastatic M+ HEp3 cells compared to the congenic and low metastatic variant, M-HEp3. In addition, the noncongenic prostate cancer cell lines PC-3 and LNCaP showed a similar trend; the former, a metastatic cell line, showing much higher levels of SIMA135 compared to the latter, a low metastatic cell type (Soos et al., 1997).

The observation of apparently free SIMA135 in glandular mucus of both normal and malignant glands (FIG. 6) is consistent with the observation that a 10 kDa soluble form of this protein is released in vitro by HEp3 cells. The distinct loss of glandular tissue ultrastructure that is apparent during tumorigenesis may permit the release of the soluble form of SIMA135/CDCP1 into the fluid and vascular system of the colon cancer patient. Accordingly, SIMA135 is thought to have utility as a serum or tissue fluid marker as has been proposed for the transmembrane proteins MUC1 (Rye and McGuckin, 2001), CD44 (Adham et al., 1990) and ICAM-1 (Maruo et al., 2002).

I. SIMA135, Fragments, and Variants Thereof that are Glycosylated or Non-Glycosylated.

The invention provides the SIMA135 protein, fragments of SIMA135, and variants of SIMA135 that can be glycosylated or non-glycosylated. These proteins, fragments, and variants of SIMA135 can be used as antigens to induce production of antibodies that bind to SIMA135.

These proteins, fragments, and variants can also be used to select for antibodies that specifically and selectively bind to SIMA135. Such specifically and selectively binding antibodies include those that bind to SIMA135, or a portion of SIMA135, but that do not bind to proteins and fragments of proteins that are not SIMA135, or a fragment of SIMA135. In particular, the selectivity of such antibodies means that they bind to SIMA135 or a portion of SIMA135 but do not also bind to the 180 kD protein produced from metastatic Hep-3 cell lysate as described in U.S. Pat. No. 6,498,014 with a dissociation constant of the same order of magnitude as that resulting from binding to SIMA135 or a fragment thereof, although binding of such antibodies with the 180 kD protein may occur at a dissociation constant at least two orders of magnitude greater than that for binding with SIMA135 or a fragment thereof. The specificity of such antibodies means that the immunogenic binding is the result of epitopal—hypervariable region interaction and not the result of non-specific protein—protein interaction. Non-specific protein—protein interaction typically will have a dissociation constant at least 3 orders of magnitude greater than the dissociation constant for the specific binding of an epitopal—hypervariable region interaction. The dissociation constant for an antibody—antigen immunobinding pair can be measured according to the techniques described in Harlow et al., Antibodies: A Laboratory Manual, (Cold Spring Harbor Pub. 1988)), which is hereby incorporated by reference.

A fragment of a SIMA135 protein as used herein, refers to a peptide fragment of a sufficient length to be antigenic. Generally speaking, the fragment includes at least 5 amino acids.

Variant proteins include proteins having amino acid substitutions that are biologically active, or that elicit antibody production when used as an antigen. A variant of SIMA135 is intended to include a protein derived from native SIMA135 by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the SIMA135 proteins of the invention may be altered in various ways including amino acid substitutions, deletions, truncations, and insertions. Methods for such manipulations are generally known in the art. For example, amino acid sequence variants of the polypeptides can be prepared by mutations in DNA encoding SIMA135. Methods for mutagenesis and nucleotide sequence alterations are well known in the art. See, for example, Kunkel, Proc. Natl. Acad. Sci. USA, 82, 488 (1985); Kunkel et al., Methods in Enzymol., 154:367 (1987); U.S. Pat. No. 4,873,192; Walker and Gaastra, eds., Techniques in Molecular biology, MacMillan Publishing Company, New York (1983) and the references cited therein. Guidance as to appropriate amino acid substitutions that do not affect biological activity of the protein of interest may be found in the model of Dayhoff et al., Atlas of Protein Sequence and Structure, Natl. Biomed. Res. Found., Washington, D.C. (1978), herein incorporated by reference. Conservative substitutions, such as exchanging one amino acid with another having similar properties, are preferred.

Conservative amino acid substitutions are preferred and include, for example; aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. Members in each group can be substituted for one another. For example, a group of amino acids having aliphatic side chains is glycine, alanine, valine, leucine, and isoleucine. These may be substituted for one another. A group of amino acids having aliphatic-hydroxyl side chains is serine and threonine. A group of amino acids having amide-containing side chains is asparagine and glutamine. A group of amino acids having aromatic side chains is phenylalanine, tyrosine, and tryptophan. A group of amino acids having basic side chains is lysine, arginine, and histidine. A group of amino acids having sulfur-containing side chains is cysteine and methionine. For example, replacement of a leucine with an isoleucine or valine, an aspartate with a glutamate, a threonine with a serine, or a similar replacement of an amino acid with a structurally related amino acid may be accomplished to produce a variant polypeptide of the invention.

The proteins of the invention may be glycosylated or not glycosylated. The proteins may be glycosylated in vivo by expressing the proteins in a cell that is able to glycosylate the recombinant protein. Alternatively, the proteins of the invention can be glycosylated in vitro through use of sugar transferases. The proteins may be treated to cleave any linked glycans through use of commercially available enzymes, for example PNGase F (New England Biolabs, Beverly, Mass.). Accordingly, the proteins of the invention can be used to produce antibodies that bind to native SIMA135, denatured SIMA135, specific portions of SIMA135, glycosylated SIMA135, and to non-glycosylated SIMA135.

II. An Antibody that Selectively Binds to SIMA135, or to a Fragment of SIMA135.

The invention provides antibodies that bind to SIMA135. Preferred antibodies to be used in pharmaceutical compositions include those antibodies that inhibit tumor metastasis. Inhibition of tumor metastasis can be determined by a number of assays, such as the migration assay, the invasion assay or the chick chorioallantoic membrane assay.

Antibodies can be prepared that recognize natively folded SIMA135, or denatured SIMA135 by immunizing an animal with native SIMA135 or denatured SIMA135 respectively. In addition, antibodies can be prepared that recognize SIMA135 that is glycosylated, or SIMA135 that is not glycosylated by immunizing an animal with SIMA135 that is glycosylated or non-glycosylated respectively. Antibodies that recognize various forms of SIMA135 (for example, native vs. denatured, and glycosylated vs. non-glycosylated) are useful for determining if a cell is able to properly fold and glycosylate SIMA135. Such antibodies are useful for determining if a candidate agent is able to interfere with cellular actions that process SIMA135 during metastasis. Accordingly, such antibodies may be used to identify the action of agents that can be used to inhibit metastasis by cancer cells.

Antibodies that bind to SIMA135, fragments of SIMA135, and variants of SIMA135, can be prepared using an intact protein or fragment containing small peptides of interest as the immunizing antigen. Fragments of SIMA135 that can be used as antigens include those that produce an immune response in an animal. These fragments will generally be five amino acids or greater in length. The protein or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled protein or peptide is then used to immunize the animal (e.g., a mouse, a rat, or a rabbit). The monoclonal antibody 41-2 is an antibody that was initially employed to isolate SIMA135. It recognizes SIMA135 and in addition several other metastasis proteins including the 180 kD protein described in U.S. Pat. Nos. 6,245,898 and 6,498,014. For this reason, a monoclonal antibody that selectively and specifically binds with SIMA135 but not with other metastasis proteins is preferred.

If desired, polyclonal or monoclonal antibodies can be purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (Coligan, et al., Unit 9, Current Protocols in Immunology, Wiley Interscience, 1991, incorporated by reference).

An antibody suitable for binding to a protein of the invention is specific for at least one portion of a region of the protein. For example, one of skill in the art can use a protein or peptide to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art (Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference).

The preparation of monoclonal antibodies likewise is conventional (Kohler & Milstein, *Nature,* 256:495 (1975); Coligan et al., sections 2.5.1-2.6.7; and Harlow et al., Antibodies: A Laboratory Manual, page 726 (Cold Spring Harbor Pub. 1988)), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992)). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an air reactor, in a continuous stirrer reactor, or immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristine tetramethylpentadecane prior to injection.

After one to three weeks, the desired monoclonal antibody is recovered from the body fluid of the animal.

An antibody of the invention may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described (Orlandi et al., *Proc. Nat'l Acad. Sci. USA*, 86:3833 (1989) which is hereby incorporated in its entirety by reference). Techniques for producing humanized monoclonal antibodies are described (Jones et al., *Nature*, 321:522 (1986); Riechmann et al., Nature, 332:323 (1988); Verhoeyen et al, *Science*, 239:1534 (1988); Carter et al., *Proc. Nat'l Acad. Sci. USA*, 89:4285 (1992); Sandhu, *Crit. Rev. Biotech.*, 12:437 (1992); and Singer et al., *J. Immunol.*, 150:2844 (1993), which are hereby incorporated by reference).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described (Green et al., *Nature Genet.*, 7:13 (1994); Lonberg et al., *Nature*, 368:856 (1994); and Taylor et al., *Int. Immunol.*, 6:579 (1994), which are hereby incorporated by reference).

Antibody fragments of the invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described (Goldenberg, U.S. Pat. Nos. 4,036,945 and 4,331,647; and references contained therein; Porter, *Biochem. J.*, 73:119 (1959); Edelman et al., Methods in Enzymology, Vol. 1, page 422 (Academic Press 1967); and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments include, an association of $V_H$ and $V_L$ chains. This association may be noncovalent (Inbar et al., *Proc. Nat'l Acad. Sci. USA*, 69:2659 (1972)). Alternatively, the variable chains can be linked by an intermolecular disulfide bond or cross-linked by chemicals such as glutaraldehyde (Sandhu, supra). Preferably, the Fv fragments comprise $V^H$ and $V^L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described (Whitlow et al., Methods: A Companion to Methods in Enzymology, Vol. 2, page 97 (1991); Bird et al., *Science*, 242:423 (1988), Ladner et al., U.S. Pat. No. 4,946,778; Pack et al., *Bio/Technology*, 11:1271 (1993); and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., Methods: A Companion to Methods in Enzymology, Vol. 2, page 106 (1991)).

III. A Method to Treat a Metastatic Tumor and to Inhibit Metastasis by a Tumor Cell.

The invention also includes methods of treating metastatic tumors. "Treating a metastatic tumor" means that the metastasis of the tumor is prevented, delayed, or inhibited. Metastatic tumors include both tumors at the primary site capable of metastasizing and metastasized tumors at a secondary site. Such metastatic tumors can be of a tissue origin of the lung, liver, kidney, mammary gland, epithelial, thyroid, leukemic, pancreatic, endometrial, ovarian, cervical, skin, colon and lymphoid tissue.

A subject which can be treated can be any mammalian subject, including humans, dogs, monkeys, cows and the like, with the exception of mice.

One embodiment of the present invention provides methods of treating a metastatic tumor in a subject by administering to the subject a therapeutically effective amount of a tumor metastasis-inhibiting antibody of the present invention. Tumor metastasis-inhibiting antibodies of the present invention have been described hereinabove. Preferred tumor metastasis-inhibiting antibodies include those antibodies that selectively bind to SIMA135, or a fragment thereof.

A tumor metastasis-inhibiting antibody can be administered alone or together with a pharmaceutically acceptable carrier. A pharmaceutically acceptable carrier includes all solvents, such as fats, oils, water, saline solutions, lipids, liposomes, resins, binders, fillers, dispersion media, cell culture media, and the like, or combinations thereof, that are non-toxic to the recipient subject.

In accordance with the present invention, the active ingredients can be combined with the carrier in any convenient and practical manner, e.g., by solution, suspension, emulsification, admixture, encapsulation, absorption and the like, and if necessary, by shaping the combined compositions into pellets or tablets. Such procedures are routine for those skilled in the art.

Dosages of an antibody to be therapeutically effective depend on the disease state and other clinical factors, such as weight and condition of the subject, the subject's response to the therapy, the type of formulations and the route of administration. The precise dosage of a compound to be therapeutically effective can be determined by those skilled in the art. As a general rule, the therapeutically effective dosage of an antibody can be in the range of about 0.5 µg to about 2 grams per unit dosage form. A unit dosage form refers to physically discrete units suited as unitary dosages for mammalian treatment: each unit containing a predetermined quantity of the active material calculated to produce the desired therapeutic effect in association with any required pharmaceutical carrier. The methods of the present invention contemplate single as well as multiple administrations, given either simultaneously or over an extended period of time.

The administration of a tumor metastasis-inhibiting antibody may be carried out in any convenient manner, including by aerosol inhalation, injection, ingestion, transfusion, implantation or transplantation. Preferably, the antibodies of the present invention are administered to a patient by subcutaneous (s.c.), intraperitoneal (i.p.), intra-arterial (i.a.), or intravenous (i.v.) injection.

IV. A Method to Diagnose Cancer in a Mammal.

The invention also includes methods of diagnosing metastatic tumors in a subject by detecting the expression of SIMA135.

Metastatic tumors include both tumors at the primary site capable of metastasizing and metastasized tumors at a secondary site. Such metastatic tumors can be of a tissue origin of the lung, liver, kidney, mammary gland, epithelial, thyroid, leukemic, pancreatic, endometrial, ovarian, cervical, skin, colon and lymphoid tissues.

The expression of SIMA135 can be detected by using an antibody that binds to SIMA135, or a fragment of SIMA135. Both polyclonal antibodies and monoclonal antibodies can be employed.

In one embodiment, a sample is taken from the subject, e.g., a biopsy specimen taken from tissue suspected of having a metastatic tumor. Generally, the sample is treated before an assay is performed. Assays which can be employed include ELISA, RIA, EIA, Western Blot analysis, immunohistological staining and the like. Depending upon the assay used, the antigens or the antibodies can be labeled by an enzyme, a fluorophore or a radioisotope. See, e.g., Coligan et al. Current Protocols in Immunology, John Wiley & Sons Inc., New York, N.Y. (1994); and Frye et al., Oncogen 4: 1153-1157, 1987.

The treatment of the sample may vary depending on the assay that is used to detect SIMA135. For example, cells of tissue biopsy can be lysed and the cell lysates are used in e.g., Western Blot analysis. For assays such as the Whole Cell ELISA assay, cells can be washed with, e.g., PBS, and then fixed with 0.25% glutaraldehyde in PBS before the assay.

The expression of SIMA135, or a fragment of SIMA135, detected by using any of the above-described methods, is compared with the expression of the same antigen in the normal part of the tissue. A substantial increase in the level of expression of the antigen when compared with the expression in the normal tissue, is indicative of a metastatic tumor. A substantial increase means an increase of at least about 20%, preferably, at least about 25%, more preferably, at least about 35%.

In another embodiment, immunohistochemistry can be used to diagnose a metastatic tumor in an organism. In this embodiment, a sample is taken from an organism, e.g., a biopsy specimen taken from tissue suspected of having a metastatic tumor. The sample can be affixed to a slide and contacted with antibodies, as disclosed herein, that bind to SIMA135. The antibodies can be labeled by an enzyme, a fluorophore or a radioisotope. See, e.g., Coligan et al. Current Protocols in Immunology, John Wiley & Sons Inc., New. Following binding of the antibodies to SIMA135, the position of the antibodies is determined through use of known techniques. Heterologous staining, extensive expression of SIMA135 throughout the tissue sample, and staining within malignant glands in the colonic serosa indicate metastatic cancer.

V. A Kit Containing an Antibody that Selectively Binds to SIMA135, or Fragments Thereof, and Packaging Material.

The invention provides a kit containing an antibody that binds to SIMA135 and packaging material. Such kits are useful for shipping and storage of antibodies that can be used for treating and detecting cancer. Specifically, such kits may be used by medical personal in a laboratory for detecting metastatic cancer in a tissue sample obtained from an organism. Furthermore, such kits may be useful for medical personal for the formulation of pharmaceutical compositions that contain an antibody of the invention.

The packaging material will provide a protected environment for the antibody. For example, the packaging material may keep the antibody from being contaminated. In addition, the packaging material may keep an antibody in solution from becoming dry.

Examples of suitable materials that can be used for packaging materials include glass, plastic, metal, and the like. Such materials may be silanized to avoid adhesion of an antibody to the packaging material.

VI. A Pharmaceutical Composition Containing an Antibody that Selectively Binds to SIMA135, or to a Fragment of SIMA135, and a Pharmaceutically Acceptable Carrier.

A pharmaceutical composition of the invention includes an antibody that binds to SIMA135 that is formulated as a pharmaceutical composition and administered to an animal host, such as a human patient in a variety of forms adapted to the chosen route of administration, i.e., orally or parenterally, by intravenous, intramuscular, topical or subcutaneous routes.

Thus, an antibody may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the antibody may be combined with one or more excipients and used in the form of ingestible tablets, buccal tablets, troches, capsules, elixirs, suspensions, syrups, wafers, and the like. Such compositions and preparations should contain at least 0.1% of the antibody. The percentage of the compositions and preparations may, of course, be varied and may conveniently be between about 2 to about 60% of the weight of a given unit dosage form. The amount of the one or more antibodies in such therapeutically useful compositions is such that an effective dosage level will be obtained. When administered orally, the compositions of the invention can preferably be administered in a gelatin capsule.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the antibody or antibodies, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the antibody or antibodies may be incorporated into sustained-release preparations and devices.

The antibody or antibodies of the invention may also be administered intravenously or intraperitoneally by infusion or injection. Solutions of the antibody or antibodies can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the antibody or antibodies which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating an antibody or antibodies in the required amount in the appropriate solvent with various of the other ingredients enumerated above, as required, followed by filter sterilization.

VII. A Method to Identify an Agent that Modulates Production of SIMA135 by a Cell The invention provides a method to identify an agent that increases or decreases production of SIMA135 by a cell. Generally, the method involves contacting a test cell with a candidate agent and determining if production of SIMA135 by the test cell is increased or decreased relative to a control cell that was not contacted with the candidate agent.

SIMA135 production by the test cell and the control cell can be detected through use of many art recognized methods. Such methods are exemplified by immunological methods that include radioimmunoassay (RIA), enzyme-linked immunosorbant assay (ELISA), use of fluorescently labeled antibodies, and the like.

Many examples of candidate agents that can be screened according to the method are described in the official United States Pharmacopeia, official National Formulary, or any supplement to them. Briefly, examples of candidate agents include, hydrocarbons, cyclic organic molecules, bicyclic organic molecules, aryl organic molecules, alkyl organic molecules, and the like. Merck Manual, Merck Research Laboratories, Whitehouse Station, N.J. 17$^{th}$ edition, eds, Beers and Berkow 1999; Merck Index, Merck Research Laboratories, Whitehouse Station, N.J., 13$^{th}$ ed., 2001.

The metastatic HEp3 cells such as those exemplified in the following section may be used as test cells and control cells in the method of the invention. However, the method may also be practiced with cells that produce SIMA135 normally or through recombinant methods. For example, an expression construct that provides for the production of SIMA135 may be introduced into a cell that does not produce SIMA135 prior to the introduction of the expression cassette. The transformed cell may then be used within the method of the invention to identify agents that modulate SIMA135 production. The diagnostic methods described above for detection of the presence and quantity of SIMA135 can be used with such cell systems to assay the SIMA135 production by test and control cells.

The method of the invention may also be practiced in vivo. As exemplified in the following section, a candidate agent may be administered to a test animal. A tissue sample may be obtained from the test animal and SIMA135 production by cells in the tissue sample may be compared to SIMA135 production by cells in a tissue sample obtained from a control animal. An increase in SIMA135 production by the test animal relative to the control animal indicates that the candidate agent increases SIMA135 production. A decrease in SIMA135 production by the test animal relative to the control animal indicates that the candidate agent decreases SIMA135 production. The assay of the SIMA135 may be determined by any of the analytic methods given in the diagnosis section above. Numerous animals may be used within the method of the invention. Examples of such animals include rabbits, rats, mice, monkeys, and the like.

The method of the invention may be practiced in vitro. For example, test cells and control cells may be grown in tissue culture. This allows the candidate agent to be contacted with a test cell in vitro. SIMA135 production by the test cells can then be compared to SIMA135 production by control cells as described above to determine if the candidate agent increases or decreases SIMA135 production by a cell.

The in vitro and in vivo methods will determine the ability of a test agent to promote and to mimimize or prevent metastasis. Determination of promotion will identify the agent as a cancer causing or enhancing agent. This determination has practical application for the rapid identification of cancer causing agents. Determination of minimization or prevention will identify the agent as a cancer inhibiting agent. This determination has practical application for the identification of anti-cancer agents.

EXAMPLE I

Cell Lines and Hybridomas

Human cervical adenocarcinoma HeLa, fibrosarcoma HT1080, colon adenocarcinoma DLD-1 and SW480, breast adenocarcinoma MCF7, prostate adenocarcinoma PC-3, prostate carcinoma lymph node metastasis LNCaP, lung carcinoma A549 and kidney rhabdoid tumor G401 cells were obtained from the American Type Culture Collection (Rockville, Md.). Human liver cancer HuH7 and HLE, and gastric cancer MKN45 and STKM-1 cells were provided by Dr. Peter Vogt (The Scripps Research Institute, La Jolla, Calif.) and breast adenocarcinoma MDA-MB-231 cells by Dr. Liliana Ossowski (Mount Sinai School of Medicine, N.Y.). Human epidermoid carcinoma HEp3 cells, were obtained from solid tumors serially passaged on the chorioallantoic membrane (CAM) of chicken embryos (Testa, 1992; Brooks et al., 1993). The metastatic variant of HEp3 cells, M+ HEp3, was cultured for less than 20 days before use. The low metastatic variant, M− HEp3, was maintained in culture for at least 80 days before use. Human microvascular endothelial cells (HEC) and dermal fibroblasts (HDF) were obtained from Clonetics (San Diego, Calif.) and maintained in EGM-2 MV and FGM-2 media (Clonetics) respectively. Cancer cell lines were maintained as monolayer cultures in DMEM (Invitrogen, Carlsbad, Calif.) supplemented with 10% FBS (HyClone, Logan, Utah), sodium pyruvate, penicillin/streptomycin and non-essential amino acids (Invitrogen) and grown in a humidified 5% $CO_2$ atmosphere at 37° C. Hybridomas producing MoAb 41-2 were generated by a previously described subtractive immunization approach (Brooks et al., 1993). Hybridoma culturing and purification of mAbs were performed by the Protein and Nucleic Acids Core Facility of The Scripps Research Institute using standard procedures.

EXAMPLE II

Reagents

Protease inhibitors, normal mouse IgG, anti-FLAG M2 mAb, DAB reagent and Gill hematoxylin were purchased from Sigma (St. Louis, Mo.). Reverse transcription and PCR reagents and the pCR-II Topo vector were from Invitrogen. PP2 was obtained from Calbiochem (La Jolla, Calif.).

EXAMPLE III

Protein Purification, Peptide Sequencing and Protein Analysis

Immunoprecipitations were performed on lysates from either unlabelled or $^{35}$S-labelled HEp3 cells ($5 \times 10^7$). Metabolic labeling was performed overnight in methionine/cysteine free DMEM containing Tran $^{35}$S-label (100 μCi/ml; ICN, Costa Mesa, Calif.). Cells were washed thoroughly with PBS then lysed in a buffer containing 0.1 M Tris (pH 8.0), 0.1% Triton X-100, 150 mM NaCl, 5 mM EDTA, 10 μM trans-epoxysuccinyl-L-leucylamido (4-guanidino) butane, 20 μg/ml soybean trypsin inhibitor and 25 μg/ml aprotinin. Lysates were pre-cleared against protein G-Sepharose (Pharmacia Biotech, Piscataway, N.J.) at 4° C. for 30 minutes then incubated overnight at 4° C. with 20 μg of either mAb 41-2 or, as control, nmIgG. Immunocomplexes was precipitated using protein G-Sepharose and complexes were denatured by boiling in reducing SDS loading buffer before analysis by polyacrylamide gel electrophoresis. For 35S-labelled proteins, the gel was dried and exposed to film at −80° C. Otherwise proteins were transferred to polyvinylidine difluoride (PVDF) membranes (Millipore, Bedford, Mass.). The predominant coomassie stained band, at 135 kDa, was excised then digested with trypsin. The resulting peptides were separated by high pressure liquid chromatography and sequenced on a Procise 494 protein sequencer (Applied Biosystems, Inc., Foster City, Calif.). Trypsin digestion and peptide sequencing were performed by the Protein and Nucleic Acids Core Facility of The Scripps Research Institute. Peptide sequences were used to search the GenBank database using algorithms available at the National Center for Biotechnology Information (NCBI) website. The complete SIMA135 protein sequence was analyzed for structural domains, cellular processing signals and consensus post-translational modification motifs using the Prosite database (Falquet et al., 2002), the SMART algorithm (Schultz et al., 1998), the PSORT algorithm (Nakai and Kanehisa, 1992) and the NetPhos 2.0 algorithm (Blom et al., 1999).

EXAMPLE IV

Expression Constructs and Transient Transfections

SIMA135 cDNA in the eukaryotic expression vector pME18S-FL3 (GenBank accession number AK026622) was generated as part of the Japanese NEDO human cDNA sequencing project and kindly provided by Dr. Hiroko Hata (Dept. of Virology, Institute of Medical Science, University of Tokyo). The SIMA135FLAGin construct was generated by PCR placing sequences encoding the FLAG epitope (DYKDDDDK; SEQ ID NO: 10) immediately before the stop codon of the parent construct. Both constructs were sequenced. HeLa cells ($4 \times 10^5$) were transiently transfected with either the SIMA135 or SIMA135FLAGin expression constructs using Superfect reagent (Qiagen, Valencia, Calif.) as described by the manufacturer. Cells were lysed in ice cold buffer containing 10 mM Tris (pH 8.0), 150 mM NaCl, 1% Triton X-100, 5 mM EDTA and 1× Complete mini EDTA-free protease inhibitor cocktail (Roche, Indianapolis, Ind.). Insoluble material was removed by centrifugation at 14000 rpm for 10 min.

EXAMPLE V

Cloning of the SIMA135 cDNA from HEp3 Cells

Total RNA was isolated using an RNeasy kit (Qiagen) and 2 μg served as template in a reverse transcription reaction using Superscript II reverse transcriptase. PCR was performed on 1 μl of the resulting cDNA using primers TCCCCACCGTCGTTTTCC (SEQ ID NO:2) and GGTTAGGAACACGGACGGGTG (SEQ ID NO:3)(designed based upon GenBank accession AK026622) and the proof reading enzyme Platinum Pfx DNA polymerase. PCR cycling conditions were 94° C. for 3 min, 30 cycles of 94° C. for 30 sec, 55° C. for 30 sec and 72° C. for 150 sec followed by a final 72° C. extension for 10 min. PCR products were gel purified (Qiagen) adenosine tailed using Platinum Taq DNA polymerase then cloned in the pCR-II Topo vector and sequenced.

EXAMPLE VI

Immunofluorescence

HeLa cells transiently transfected with the SIMA135FLAGin expression construct and HEp3 cells were plated on coverslips. After incubation for 48 hr at 37° C. cells were washed with PBS then fixed in 2% formaldehyde. HeLa cells to be incubated with anti-FLAG mAb were either not permeabilized or permeabilized by incubating in 0.5% Triton X-100 in PBS for 5 min at room temperature. Both cell types were blocked in 5% BSA in PBS. Following overnight incubation at 4° C. with either mAb 41-2 (5 μg/ml) or anti-FLAG M2 mAb (4 μg/ml) in blocking buffer, cells were washed with PBS then incubated with Alexa Fluor 546 conjugated goat anti-mouse IgG (2 μg/ml) (Molecular Probes). Labeled cells were visualized and photographed using a BioRad 1024 MRC2 scanning confocal imaging system.

EXAMPLE VII

Northern Blot Analysis

A human 12 lane multiple tissue Northern blot (Clontech) was hybridized with [α-$^{32}$P]dCTP labeled (Ambion) EcoRI/HincII DNA insert fragments of the SIMA135 cDNA overnight in UltraHyb solution (Ambion) at 68° C. The blot was washed to a final stringency of 0.1×SSC, 0.1% SDS at 68° C. then exposed to film at −80° C. Blots were reprobed with 13-actin cDNA to determine consistency of RNA loading in each lane.

EXAMPLE VIII

Western Blot Analysis

Cell lysates, serum free conditioned media and immunoprecipitated proteins were separated by electrophoresis through 8% SDS-polyacrylamide gels then transferred to nitrocellulose membranes (Millipore). Membranes were blocked in 5% non-fat skim milk powder in PBS then incubated overnight at 4° C. with either mAb 41-2 (2 μ/ml), anti-FLAG M2 mAb (0.8 μg/ml) or anti-phosphotyrosine mAb (1 μg/ml; Upstate Biotechnology, Lake Placid, N.Y.). Following extensive washing membranes were incubated for 2 hr at room temperature with goat anti-mouse IgG (0.16 μg/ml, Pierce, Rockford, Il) and immunoreactive bands detected by enhanced chemiluminescence (Pierce).

EXAMPLE IX

Biochemical Characterization Procedures

For removal of N-linked glycans, lysates (50 μl) from M+ HEp3 cells and HeLa cells transiently transfected with the SIMA135FLAGin expression construct were denatured and reduced in 0.5% SDS, 1% β-mercaptoethanol for 10 minutes at 100° C. then incubated with PNGase F (New England Biolabs, Beverly, Mass.) at 37° C. for 45 minutes. For analysis of the basal level of tyrosine phosphorylation of SIMA135, subconfluent cultures of HEp3 and HeLa (as negative control) cells were incubated at 37° C. for 30 min with serum free DMEM containing 50 mM NaF and 1 mM $Na_3VO_4$ then washed with ice cold PBS. For inhibition of Src kinase family phosphorylation, HEp3 cells were cultured in serum free DMEM without NaF and $Na_3VO_4$ for 30 minutes at 37° C. with PP2 (50 μM). Cells were then lysed in ice cold buffer containing 50 mM Tris (pH 7.4), 150 mM NaCl, 1% Triton X-100, 1 mM phenylmethylsulfonyl fluoride, 1 mM benzamidine, 25 μg/ml aprotinin, 25 μg/ml leupeptin, 50 mM NaF and 1 mM $Na_3VO_4$. Insoluble material was removed by centrifugation at 14000 rpm for 10 min. Immunoprecipitation was performed as described above on 300 μg of cell lysates using 1 μg of either mAb 41-2 or nmIgG (as negative control). For assays for the presence of soluble SIMA135, HEp3 cells approaching confluence, were washed three times with PBS then incubated in serum free conditioned media for 24 hr. The media was collected and centrifuged at 4° C. and 10,000 g then concentrated 10 fold using micron centrifugal filters with a molecular weight cut off of 30,000 kDa (Millipore). Cells lysates were collected as described above.

EXAMPLE X

Immunohistochemistry

Cryostat sections (6 μm) from archival human adenocarcinoma colon tissue samples from three patients were fixed in zinc-formalin for 15 min, rinsed briefly with PBS then nonspecific binding sites blocked by incubating in PBS containing 3% BSA. mAb 41-2 (5 μg/ml) was applied at 4° C. overnight. Specific antibody binding was detected by the addition of biotin conjugated anti-mouse antibodies (Pierce) followed by peroxidase conjugated neutravidin (Pierce) which was visualized using DAB reagent. Sections were counterstained using Gill hematoxylin.

Figure 1B:
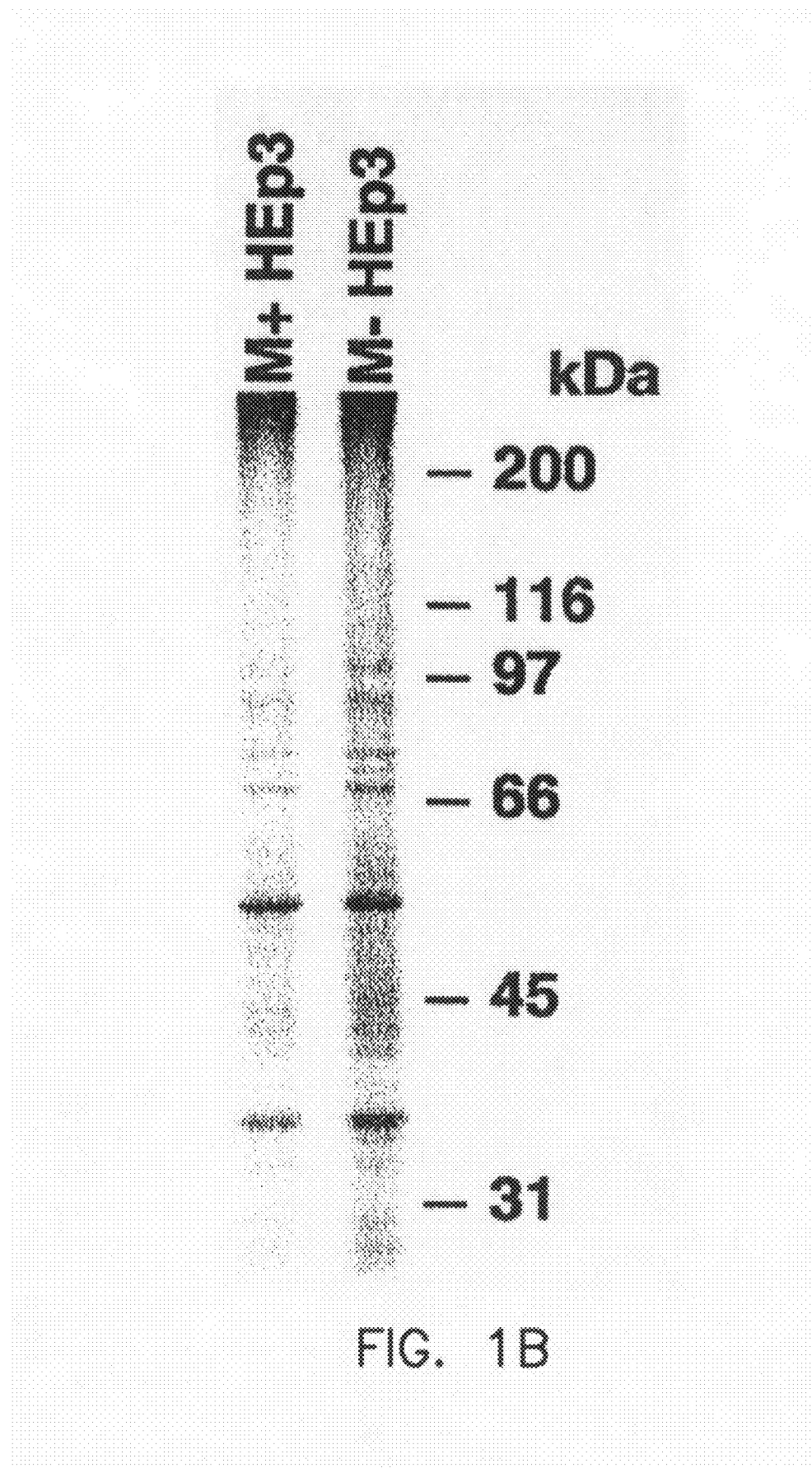
FIG. 1(B) shows coomassie stained gels of the lysates shown in FIG. 1(A) indicating that the overall protein pattern and content was indistinguishable for $M^+$ and $M^-$ HEp3 cell extracts.

EXAMPLE XI mAb 41-2 Recognizes a 135 kDa Antigen Expressed at Elevated Levels in Highly Metastatic Human Tumor HEp3 Cells The antigen recognized by the antibody mAb 41-2 was identified and characterized. As an initial step in determining the significance of the antigen recognized by mAb 41-2, Western blot analysis was performed on lysates prepared from $M^+$ and $M^-$ HEp3 cells. As shown in FIG. 1 (left panel), mAb 41-2 detected a single band of approximately 135 kDa in both cell types. Consistent with the subtractive immunization approach taken in generating mAb 41-2, the immunoreactive protein was expressed at higher levels in $M^+$ than in $M^-$ HEp3 cells. A parallel gel demonstrated that the overall protein pattern and content was indistinguishable for $M^+$ and $M^-$ HEp3 cell extracts (FIG. 1, right panel). The difference in mAb 41-2 immunoreactivity shows a significant difference in the level of expression of the cognate antigen between the two cell lines.

EXAMPLE XII

Figure 2A:
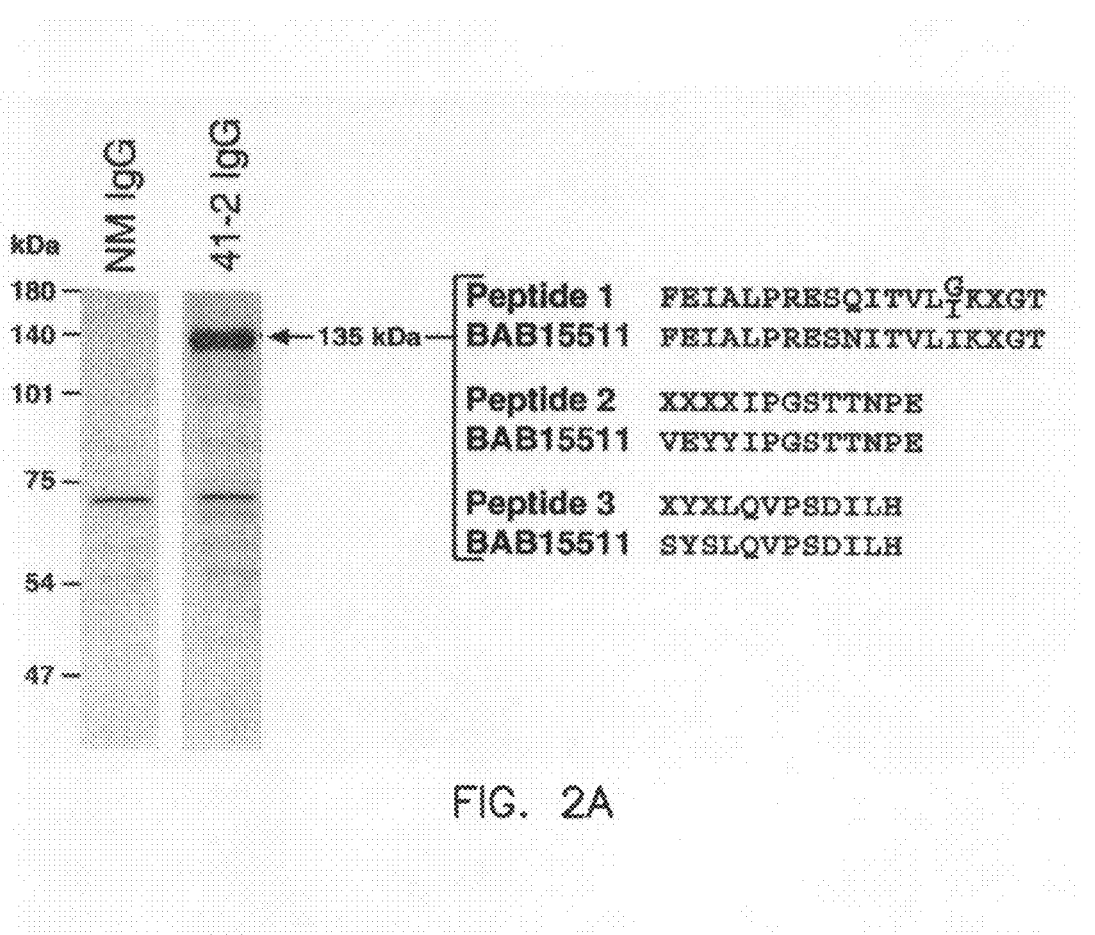
FIG. 2(A) shows SDS-PAGE analysis under reducing conditions of $^{35}S$ labeled proteins immunoprecipitated from $M^+$HEp3 cells with mAb 41-2 or normal mouse IgG (nmIgG). The gel was dried and exposed to film at −80° C. overnight. The sequence of 3 tryptic peptide fragments obtained from the excised 135 kDa protein band are indicated and aligned against peptides from GenBank entry BAB15511 (SEQ ID NOs:4-9).

Identification of the Antigen Recognized by mAb 41-2 from Metastatic HEp3 Cells Purified mAb 41-2 was used to immunoprecipitate the antigen of Example XI from $M^+$ HEp3 cells. The major protein immunoprecipitated from radiolabeled HEp3 cells had a molecular weight of approximately 135 kDa (FIG. 2A). This was consistent with the molecular weight of the antigen detected in Example XI. In a parallel experiment using unlabeled HEp3 cells, in which immunoprecipitated proteins were transferred to a PVDF membrane, the 135 kDa protein band was excised, subjected to trypsin digestion and the separated fragments sequenced from the N-terminus. As shown in FIG. 2A, three major peptide sequences were obtained. Searches of the GenBank non-redundant protein database indicated that each of the peptide sequences had exact or near exact matches with the theoretical sequence of an unpublished entry with accession number BAB 15511 (aligned in FIG. 2A), translated from unpublished cDNA entry AK026622.

Figure 2B:
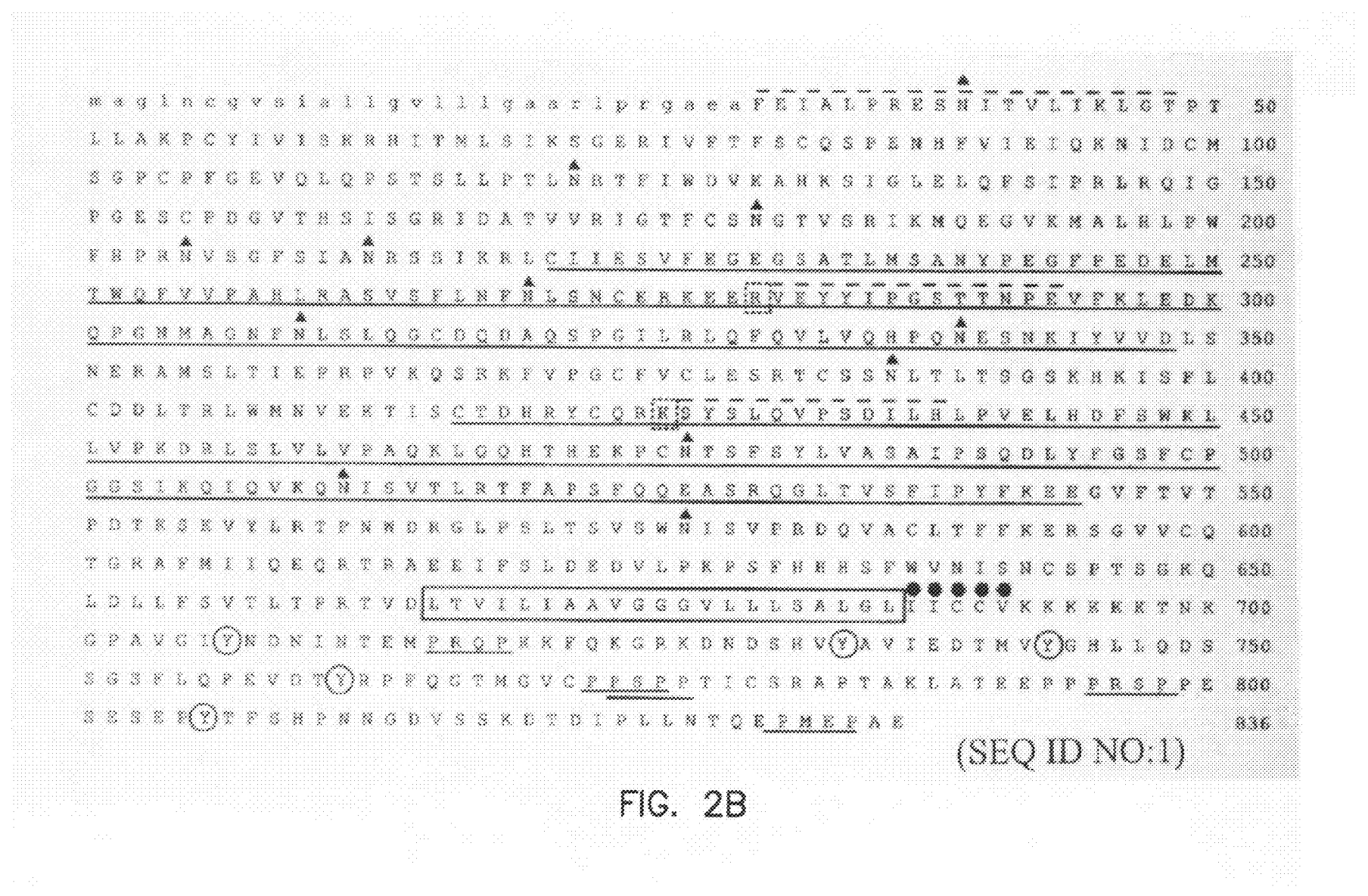
Figure 2C:
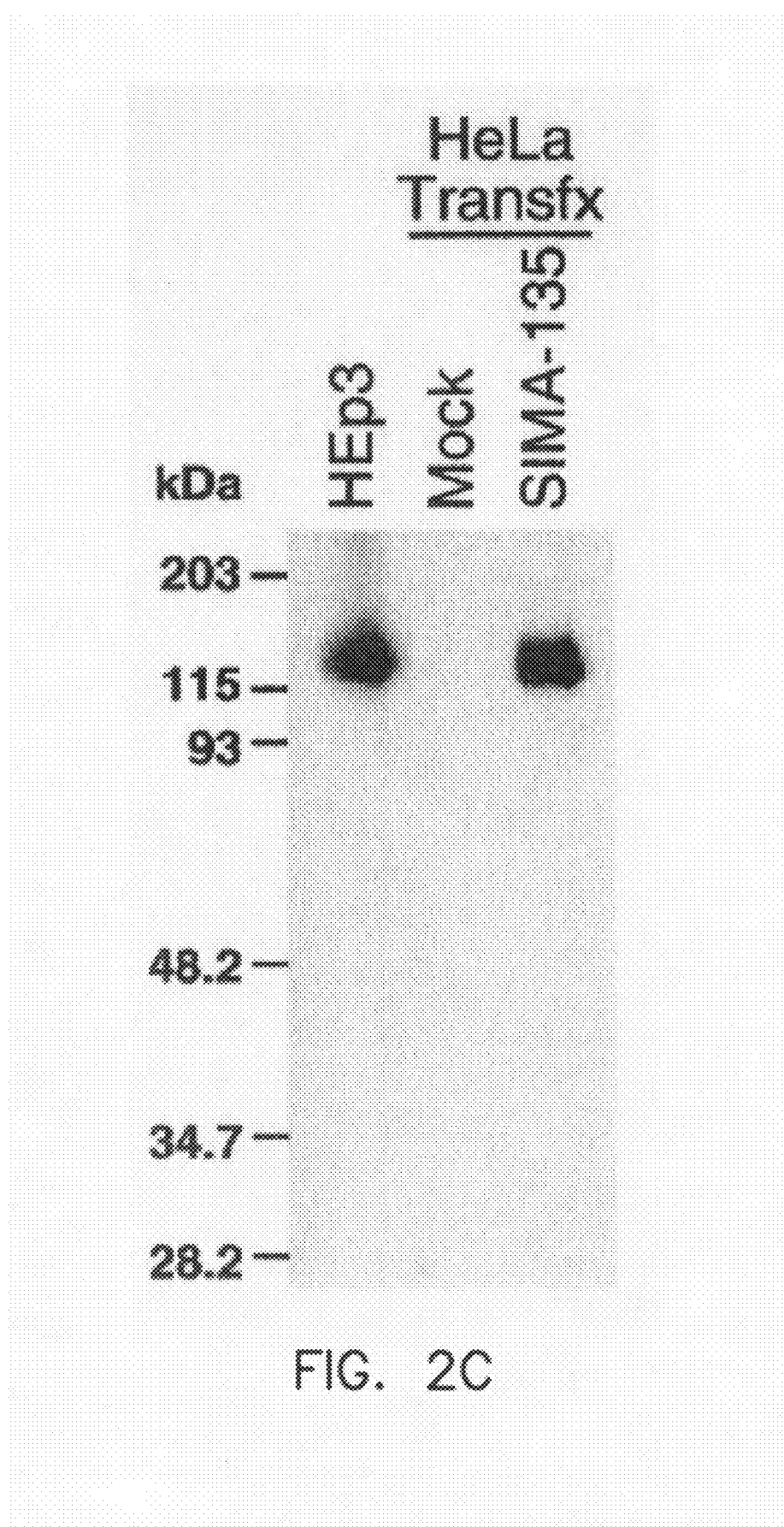
FIG. 2(C) shows western blot analysis probing with mAb 41-2 of total cell lysates (25 μg) electrophoresed under non-reducing conditions from HEp3 cells, mock transfected HeLa and HeLa cells transiently transfected with the SIMA135 cDNA.

The complete sequence of the identified protein, which was designated subtractive immunization $M^+$ HEp3 associated 135 kDa protein (SIMA135), is shown in FIG. 2B. To confirm that SIMA135 was the same protein specifically recognized by mAb 41-2, Western blot was performed on lysates from HEp3 cells, untransfected HeLa cells and HeLa cells transiently transfected with the SIMA135 cDNA. As shown in FIG. 2C, mAb 41-2 reacted with the same 135 kDa protein band that is present in HEp3 cells and in HeLa cells transiently transfected with the SIMA135 cDNA, but is absent in the untransfected HeLa cells. To provide additional confirmation, the protein encoding region of the SIMA135 mRNA was cloned from HEp3 cells by reverse transcription-PCR. DNA sequence analysis of two clones generated by this approach confirmed that SIMA135 mRNA is expressed by these cells. Four nucleotide differences were identified between GenBank entry AK026622 and SIMA135 sequence obtained from HEp3 cells: nucleotide $1684^{G \to A}$, $1847^{T \to C}$, $2236^{G \to A}$ and $2590^{G \to A}$. The second transition is silent and the others result in amino acid changes $525^{Arg \rightarrow Gln}$, $709^{Gly \rightarrow Asp}$ and $827^{Ser \rightarrow Asn}$ respectively.

EXAMPLE XIII

SIMA135 Structural Features

The SIMA135 protein sequence includes 836 amino acids (FIG. 2B) and has a deduced molecular weight of 92.9 kDa. Sequence analysis identified the following structural features. A putative amino terminal signal peptide with cleavage predicted to occur following Ala 29. This feature is consistent with the sequence of peptide 1 (FIG. 2A) indicating that mature SIMA135, with a predicted molecular weight of 90.1 kDa, starts at Phe$^{30}$. A potential transmembrane domain, spanning residues 666 to 686 (boxed in FIG. 2B), is predicted (Hartmann et al., 1989) to orient SIMA135 with its carboxy terminus located intracellularly. Twelve consensus motifs for N-glycosylation are indicted in FIG. 2B. A consensus type 1 palmitylation motif (IICCV) (Hansen et al., 1999) is located at residues 687 to 691. Five PXXP motifs are present (FIG. 2B) which in other proteins have been shown to mediate binding to Src homology (SH) 3 domains (Pawson 1995; Mayer, 2001). Five tyrosine residues (circled in FIG. 2B) may be phosphorylation sites. Two closely spaced tyrosine residues (Tyr$^{734}$ and Tyr$^{743}$) are present in consensus motifs (YXXL/I) for SH2 domain binding (Songyang et al., 1993). SIMA135 lacked homology with other confirmed proteins in the GenBank non-redundant database. However, SIMA135 did have high homology to the theoretical protein CDCP1 as determined by translation of the reported nucleic acid sequence (Scherl-Mostageer et al., 2001). In addition, two regions of the SIMA135 protein, spanning residues 221 to 348 and 417 to 544, were identified that had low homology to CUB (complement protein subcomponents Clr/Cls, urchin embryonic growth factor and bone morphogenetic protein 1) domains (Bork and Beckmann, 1993). These domains have been reported to act in mediating protein-protein interactions (Chen and Wallis, 2001; Sieron et al., 2000). A third putative CUB domain described by Scherl-Mostageer and co-workers spanning residues 545 to 660 (Scherl-Mostageer et al., 2001) was below the homology detection threshold of the search algorithms used by us to scan the SIMA135 amino acid sequence and the theoretical amino acid sequence for CDCP1.

EXAMPLE XIV

Expression Pattern of SIMA135 in Normal and Malignant Cells and Tissues

Figure 3A:
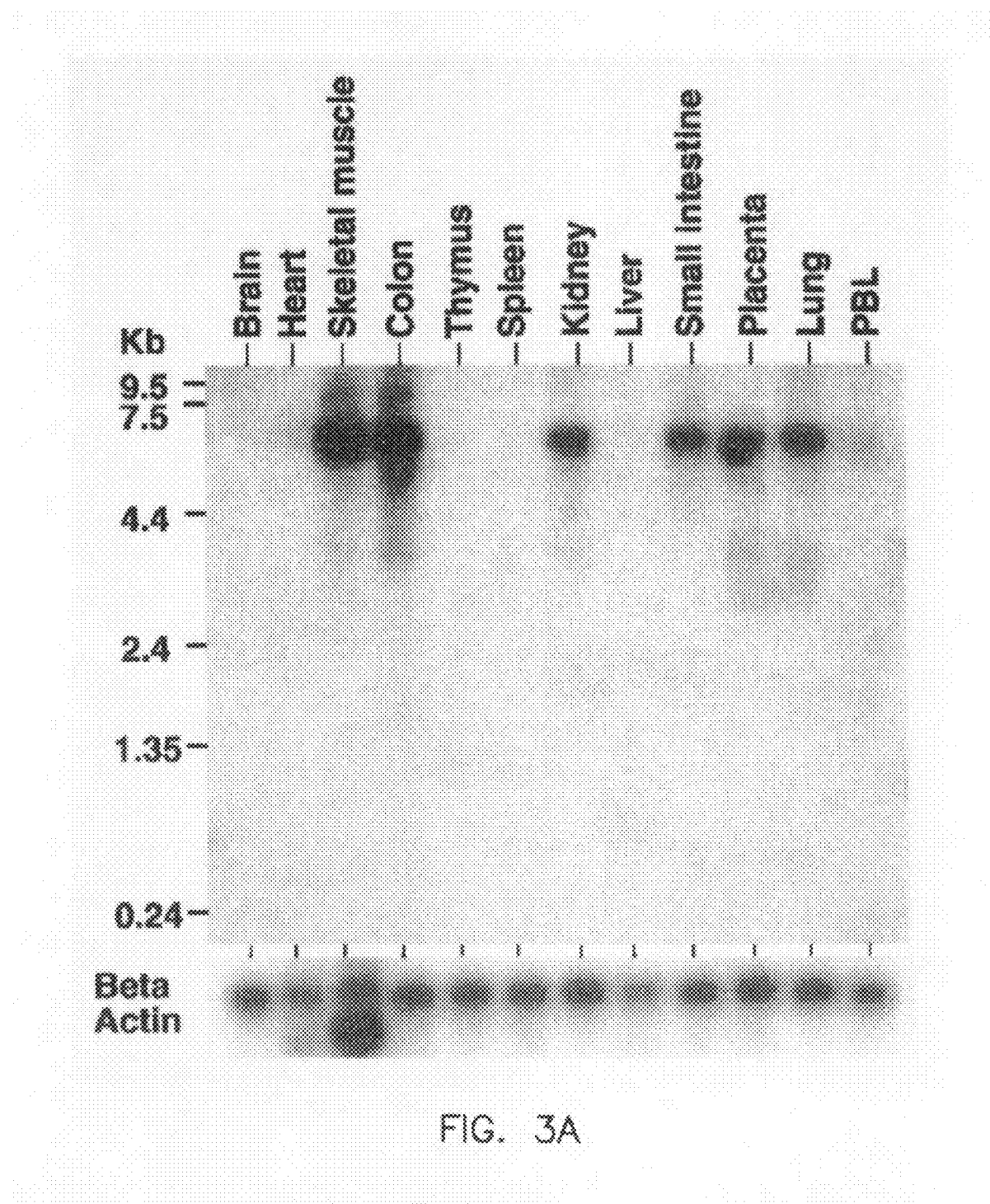
FIG. 3(A) shows northern blot analysis of poly $A^+$ RNA (1 μg per lane) from 12 normal human tissues probed with a $^{32}P$ labeled SIMA135 cDNA probe. Levels of β-actin mRNA are shown as a measure of loading.

The expression pattern of SIMA135 mRNA in 12 normal human tissues was examined by Northern blot analysis by hybridizing with a $^{32}$P-labeled 2.8 kb SIMA135 cDNA probe. A band of approximately 6.0 kb was detected at highest levels in skeletal muscle and colon with lower levels of expression in kidney, small intestine, placenta and lung (FIG. 3A). A barely detectable signal at ~6.0 kb also was present in peripheral blood leukocytes. In addition, a much weaker signal at approximately 3.3 kb was present in skeletal muscle, colon, placenta and lung. SIMA135 mRNA was not detected in brain, heart, thymus, spleen or liver. Based upon alignment of SIMA135 with CDCP1 cDNA$^7$ and genomic sequences (data not shown), it appears most likely that the two SIMA135 transcripts detected by Northern blot analysis result from use of alternate polyadenylation signals within the SIMA-135 3' UTR. The longer, more highly expressed transcript is thought to have resulted from use of a more 3' consensus poladenylation signal (at nucleotide 5950$^7$), whereas the shorter, more lowly expressed transcript likely results from use of a variant, less efficient polyadenylation signal located at nucleotide 3186$^7$. It is also possible that these variant transcripts result from alternate splicing of the SIMA135 pre-mRNA.

Figure 3B:
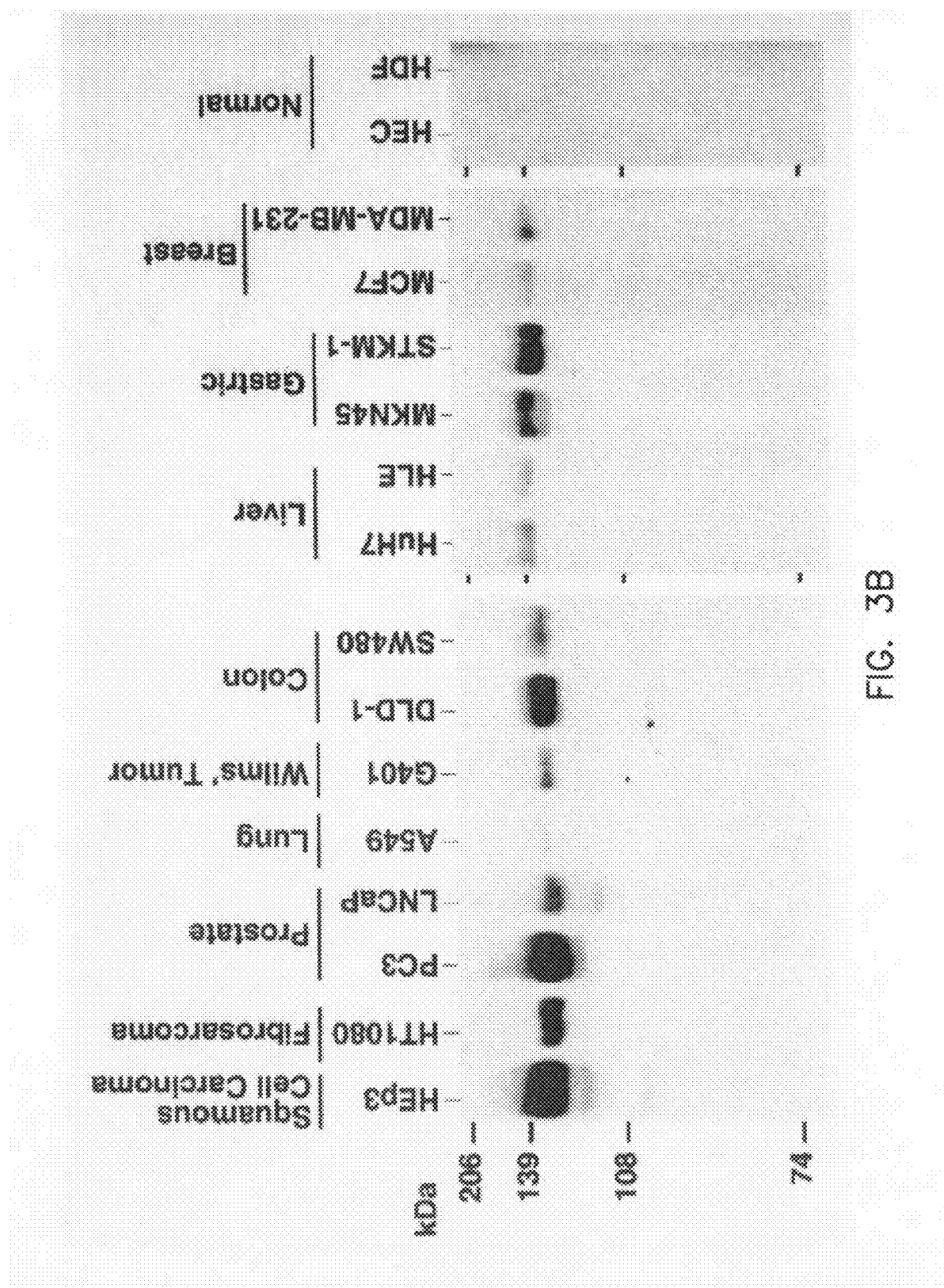
FIG. 3(B) shows western blot analysis under non-reducing conditions of whole cell lysates (20 μg per lane) from 14 human tumor cell lines and two normal human cell lines probing with mAb 41-2. HEC, microvascular endothelial cells; HDF, adult dermal fibroblasts.

SIMA135 protein expression in 16 human cell lines was analyzed by Western blot analysis in which equal amounts of cell lysate protein (20 μg) were electrophoresed for each cell line. As shown in FIG. 3B, SIMA135 was most highly expressed in metastatic HEp3 cells, with the prostate cancer cell line PC3, and the colon cancer cell line DLD-1 also manifesting high levels of expression. Moderate levels of the antigen were detected in the fibrosarcoma cell line HT1080, the gastric cancer cell lines MKN45 and STKM-1, the colon cancer cell line SW480 and the non-metastatic prostate cancer cell line LNCaP. Low levels of SIMA135 were detected in 2 liver cancer cell lines, 2 breast cancer cell lines, the lung cancer cell line A549 and the kidney rhabdoid tumor cell line G401. SIMA135 was not detectable in normal human microvascular endothelial cells and dermal fibroblast cells. Varying levels of SIMA135 protein was expressed in a number of human tumor cell lines, while two normal human cell types did not express the protein.

EXAMPLE XV

SIMA135 is a Cell Surface, Phosphorylated Glycoprotein

Figure 4A:
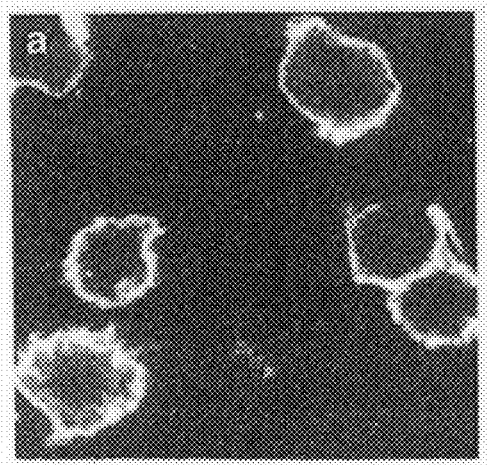
FIG. 4 shows that SIMA135 is located on the cell surface with a type I orientation. Fluorescent confocal microscopic analysis of HEp3 cells FIG. 4(A) and HeLa cells transiently transfected with the SIMA135-FLAG in expression construct FIGS. 4(B), 4(C), and 4(D). HEp3 cells were incubated with mAb 41-2 FIG. 4(A) and transiently transfected HeLa cells were incubated with either mAb 41-2 FIG. 4(B) or an anti-FLAG mAb FIG. 4(C) and FIG. 4(D). Transiently transfected HeLa cells incubated with anti-FLAG mAb in panel FIG. 4(C) had been permeabilzed using 0.5% Triton X-100 to permit access of the antibody to the intracellularly located FLAG tag. Transfected cells in panel FIG. 4(D) were not permeabilized. Magnification 600×.
Figure 4B:
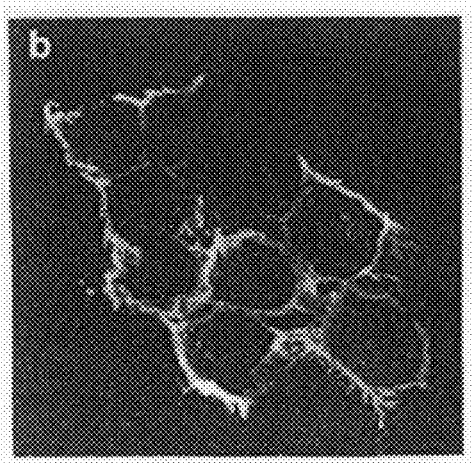
Figure 4C:
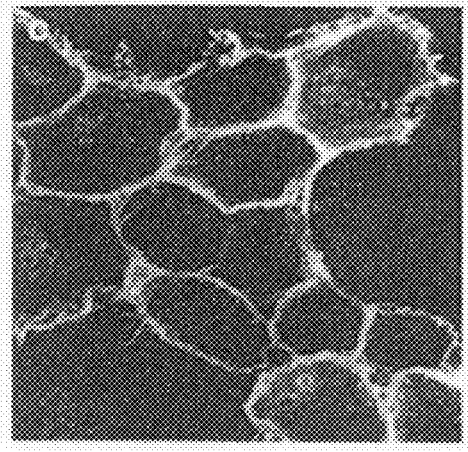
Figure 4D:
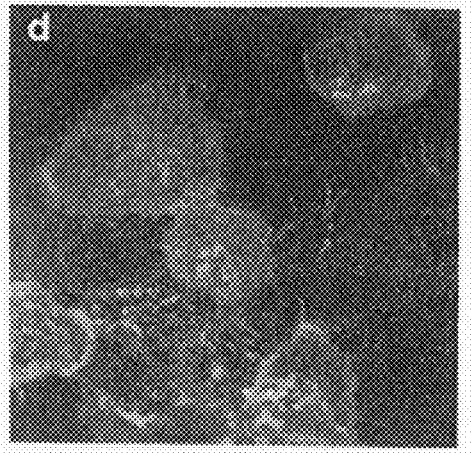

Immunocytochemistry was used to determine the cellular location of SIMA135 in HEp3 cells, and also in HeLa cells that were transiently transfected with a SIMA135 expression construct. The expression construct contained a FLAG epitope fused after the carboxy terminus of the SIMA135 protein. HEp3 cells incubated with mAb 41-2 showed strong staining on the plasma membrane (FIG. 4A). HeLa cells transiently transfected with FLAG tagged SIMA135 also showed similar strong membrane staining when incubated with mAb 41-2 (FIG. 4B). In addition, the SIMA135 carboxy terminus was determined to be intracellular as transiently transfected HeLa cells permeabilized with Triton X-100 showed strong membrane staining when incubated with an anti-FLAG epitope mAb (FIG. 4C), while non-permeabilized cells exhibited low or near background staining with anti-FLAG mAb (FIG. 4D). Untransfected HeLa cells were essentially free of staining when incubated with either mAb 41-2 or an anti-FLAG epitope mAb. These data confirmed the predicted cell surface location as well as the type I orientation of SIMA135. Also, the coincidence of staining observed with mAb 41-2 and anti-FLAG mAb in HeLa cells transiently transfected with the SIMA135-FLAG tag expression construct, additionally confirmed that SIMA135 is the target antigen for mAb 41-2.

Figure 5A:
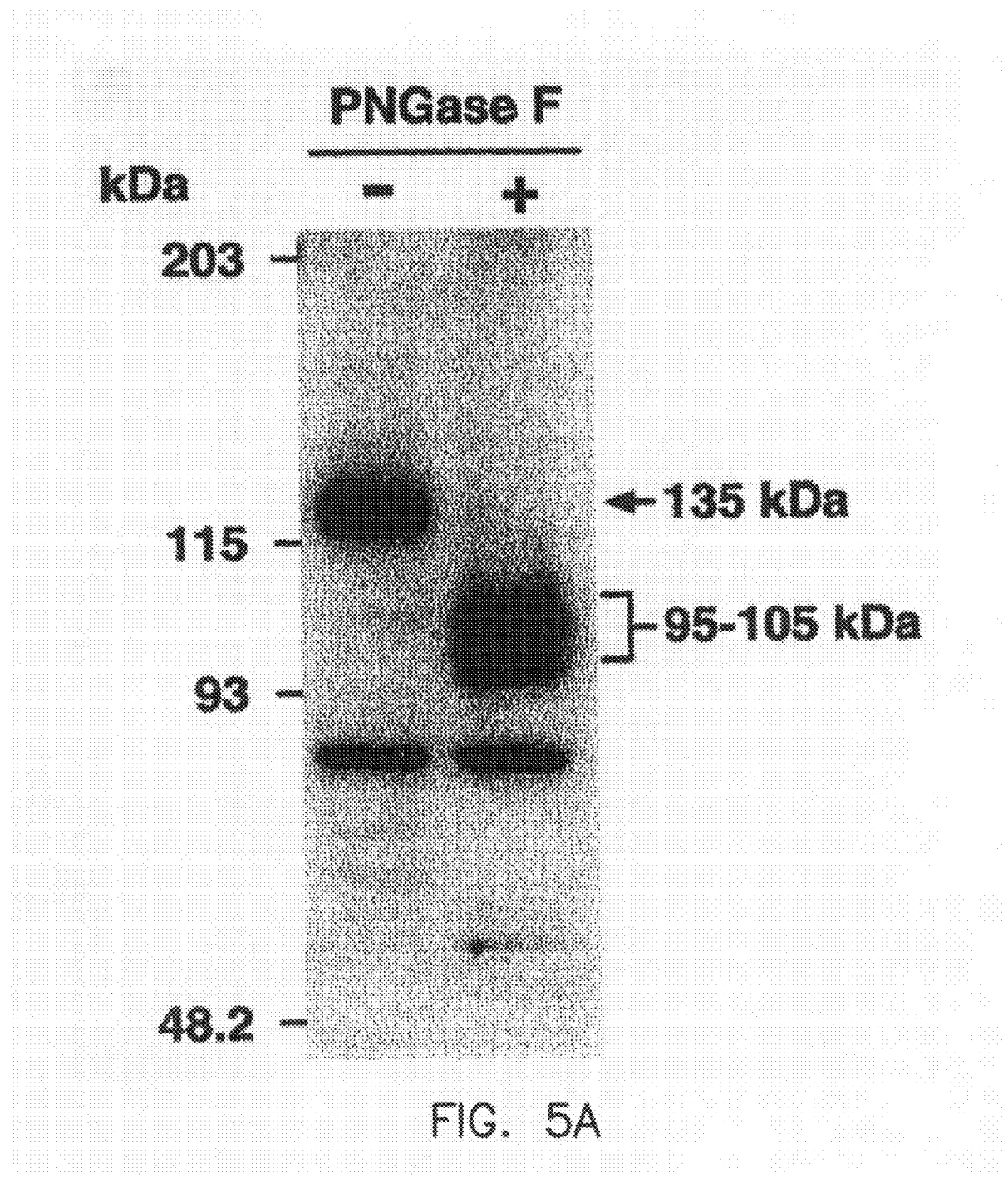
FIG. 5(A) illustrates western blot analysis under reducing conditions probing with an anti-FLAG mnAb of untreated (−) and N-glycosidase F (PNGase F) treated (+) lysates from HeLa cells transiently transfected with the SIMA135FLAGin expression construct. Bands due to SIMA135 are indicated. A non-specific cross reacting band is apparent at 80 kDa.

The theoretical molecular weight of mature SIMA135 is 90.1 kDa (FIG. 2B). However, the apparent molecular weight of the protein detected by mAb 41-2 was 135 kDa (FIGS. 1, 2C and 3B). Cell lysates from HeLa cells transiently transfected with a SIMA135 FLAG tag expression construct were treated with N-glycosidase F under conditions optimal for enzyme activity to determine if the difference in molecular weight was due to N-glycosylation. Proteins were examined by Western blot analysis using an anti-FLAG epitope mAb. N-glycosidase F treatment resulted in the disappearance of the SIMA135 protein band at 135 kDa and replacement with a broad lower molecular weight band of approximately 95 to 105 kDa (FIG. 5a). Lysates of M$^+$ HEp3 cells were also immunoprecipitated with mAb 41-2 and treated with N-glycosidase F. The proteins detected according to this method also manifested a similar diminished molecular weight. Therefore, up to 30-40 kDa of the apparent molecular weight of SIMA135 is due to N-glycosylation, consistent with the large number of consensus glycosylation sites in the extracellular region of this protein (FIG. 2B).

Figure 5B:
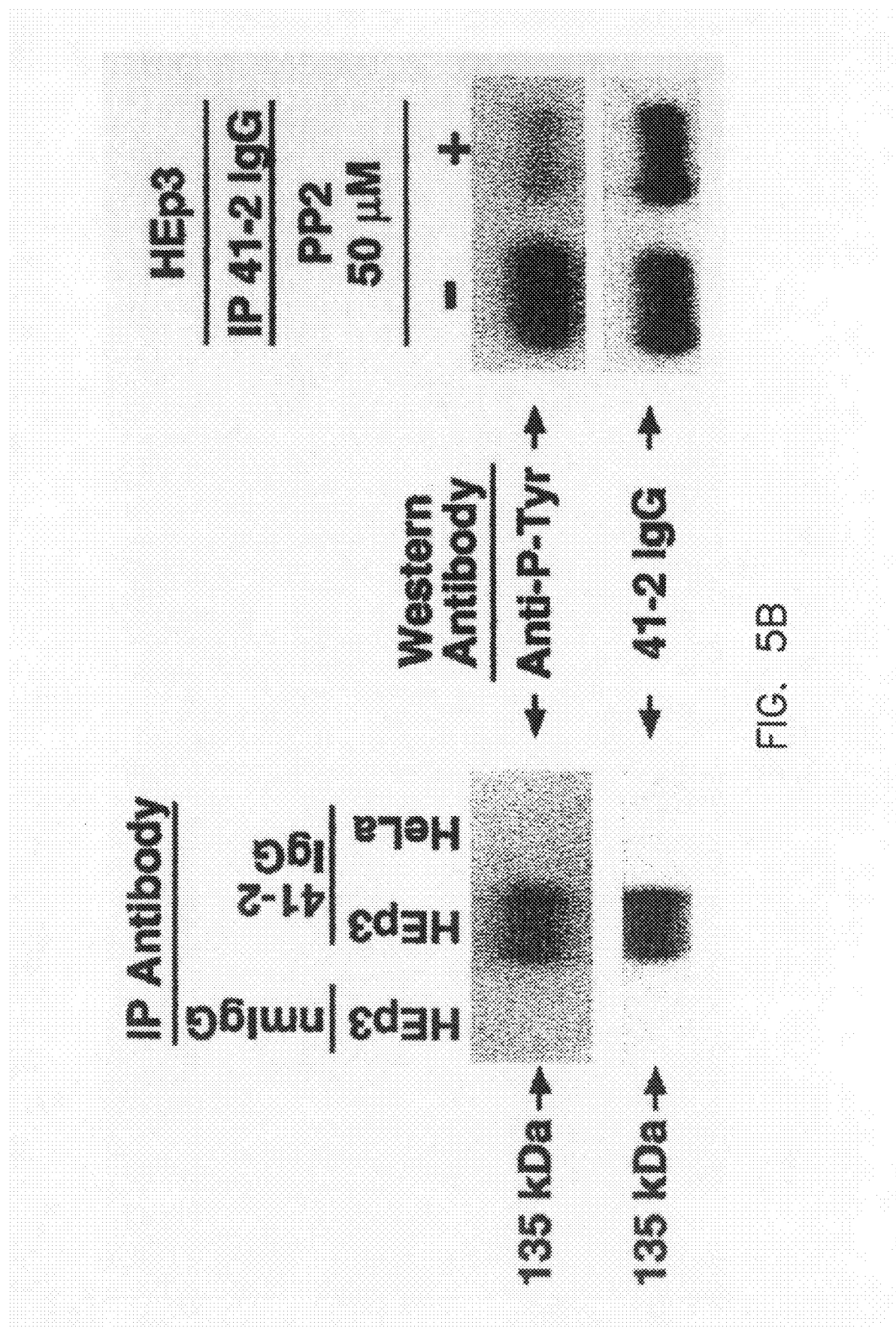
FIG. 5(B) illustrates western blot analysis under reducing conditions of immunoprecipitated proteins. The left panel of FIG. 5(B) shows immunoprecipitations that were performed with either normal mouse IgG (nmIgG) or mAb 41-2 from HEp3 and HeLa (negative control) cell lysates. Immunoprecipitated proteins were probed with an anti-phosphotyrosine antibody (Anti-P-Tyr) and with mAb 41-2 to indicate the presence of phosphorylated and total SIMA135, respectively. The right panel of FIG. 5(B) shows that cell lysate proteins were immunoprecipitated with mAb 41-2. Lysates were prepared from HEp3 cells either untreated (−) or (+) incubated for 30 minutes at 37° with PP2 (50 μM).

The intracellular region of SIMA135 contained 5 tyrosine residues (FIG. 2B). Western blot analysis with an anti-phosphotyrosine antibody was performed on proteins immunoprecipitated from HEp3 cell lysates with mAb 41-2 to determine whether any of these residues are phosphorylated. As shown in FIG. 5B (left panel), the anti-phosphotyrosine antibody detected a protein of 135 kDa that immunoprecipitated from HEp3 cells with mAb 41-2. The same protein band was detected when the immunoprecipitated proteins were probed with mAb 41-2. Western blot analysis was also performed on proteins immunoprecipitated from HeLa cell lysates with mAb 41-2, and proteins immunoprecipitated from HEp3 cell lysates with normal mouse IgG as controls. Both immunoprecipitations were free of immunoreactivity when probed with either the anti-phosphotyrosine antibody or mAb 41-2 (FIG. 5B, left panel), demonstrating the specificity of the immunoreactions observed with HEp3 cells. The involvement of a Src kinase family member in SIMA135 tyrosine phosphorylation was examined using PP2, a Src family-selective tyrosine kinase inhibitor (Hanke et al., 1996). Western blot analysis with an anti-phosphotyrosine antibody of proteins immunoprecipitated from HEp3 cell lysates with mAb 41-2, showed that HEp3 cells treated with PP2 for 30 minutes had a significant reduction (~75%) in the level of SIMA135 tyrosine phosphorylation compared to protein from untreated HEp3 cells (FIG. 5B, right panel). Western blot analysis, using mAb 41-2, of the same immunoprecipitated proteins, indicated that approximately equal amounts of SIMA135 protein were present in both lanes on the membrane (FIG. 5B right panel). These data suggested that a Src kinase family member acts during tyrosine phosphorylation of SIMA135 in HEp3 cells.

Figure 5C:
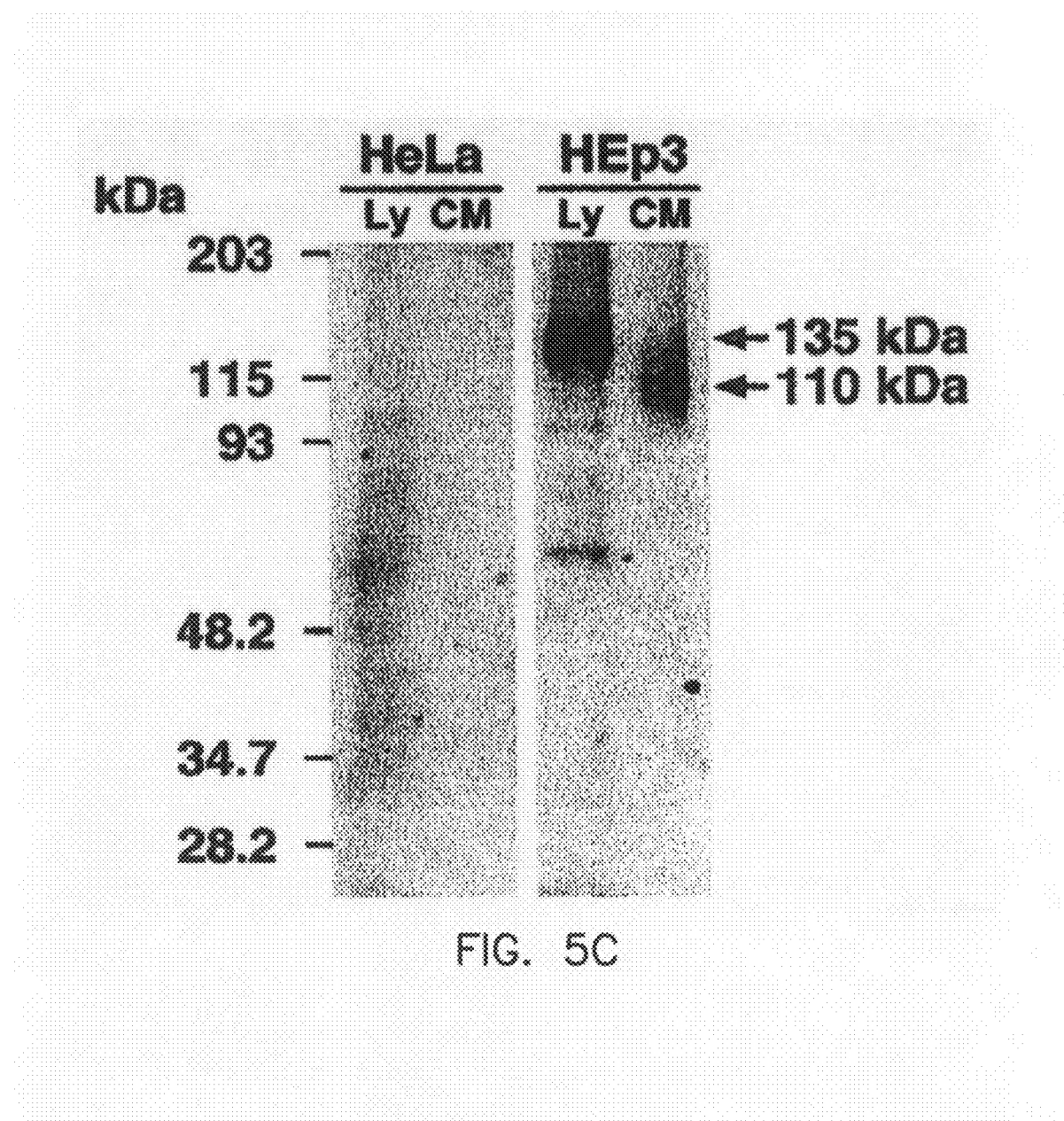
FIG. 5(C) illustrates western blot analysis under non-reducing conditions of total cell lysates (Ly, 20 μl) and centrifuged, 10× concentrated, serum free conditioned media (CM, 20 μl) probing with mAb 41-2. The 110 and 135 kDa forms of SIMA135 are indicated. HEp3 and control HeLa cells were processed and probed in an identical manner.

A number of integral cell surface proteins, such as c-met (Wajih et al., 2002) and CD44 (Goebeler et al., 1996), are also produced as soluble molecules. Western blot analysis, probing with mAb 41-2, was employed to examine whether HEp3 cells produce a soluble form of SIMA135. HEp3 cell cultures were washed extensively with PBS then incubated for 20 hr with serum-free (SF) medium. The conditioned medium (CM) was harvested and cellular material was removed by centrifugation and the media then concentrated 10 fold. The antibody mAb 41-2 detected an immunoreactive band of approximately 110 kDa in HEp3 SFCM (FIG. 5C). The cell-associated SIMA135 from HEp3 lysates was detected at 135 kDa. In contrast, untransfected HeLa cells, which do not produce SIMA135, yielded no immunoreactive bands in either the lysate or concentrated SFCM. These data indicate that HEp3 cells release a soluble form of SIMA135 and the soluble form presents as a lower molecular weight immunoreactive protein.

EXAMPLE XVI

Expression of SIMA135 in Normal and Cancerous Colon

Figure 6A:
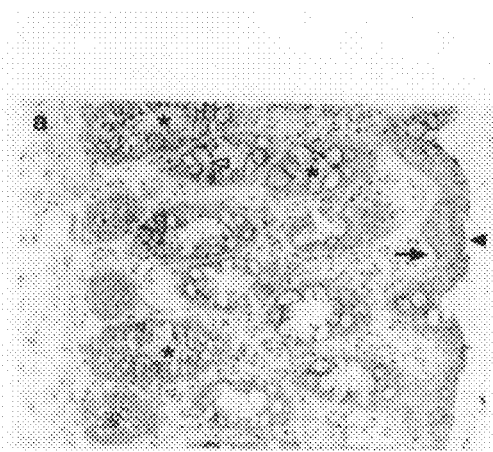
FIG. 6(A) shows representative normal colonic mucosa showing epithelial expression of SIMA135 (red-brown in color photograph). Arrowhead and right facing arrow, luminal and basal expression, respectively, on surface epithelial cells. Open arrowhead, apical expression on colonic crypt epithelial cells. Asterisk, intense staining in the contents of goblet cells and in the lumen of glands.
Figure 6B:
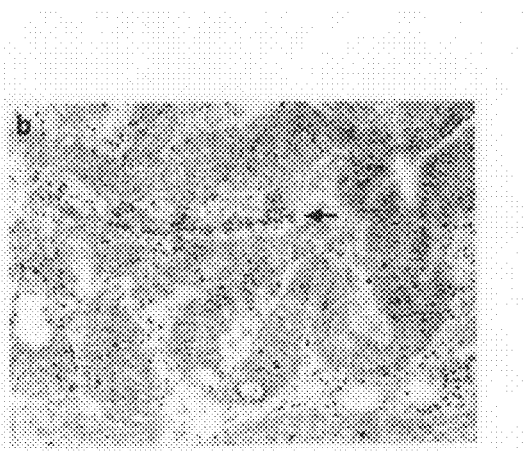
FIG. 6(B) shows that colon carcinomas display heterogeneous and extensive expression of SIMA135. Arrow, mucus staining within malignant glands.
Figure 6C:
FIG. 6(C) shows expression of SIMA135 by cells within invading malignant glands in the colonic serosa.
Figure 6D:
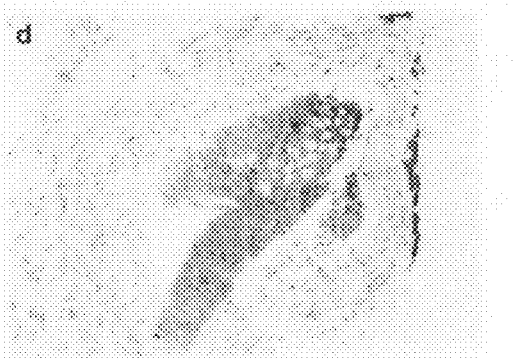
FIG. 6(D) shows expression of SIMA135 by malignant epithelial cells within the lumen of a draining blood vessel in the serosa of the colon. The magnification used in FIG. 6(A), FIG. 6(B), and FIG. 6(d) was 250×; the magnification used in FIG. 6(C) was 100×.

Immunohistochemical analysis was performed to determine the in vivo localization of SIMA135 in normal and cancerous colon. In normal colonic mucosa, SIMA135 was expressed exclusively by epithelial cells where it was present uniformly on the luminal (arrowhead) and basal (arrow) surfaces of cells lining the colonic lumen, and on the apical surfaces of cells lining the glandular crypts (open arrow) (FIG. 6A). The presence of intense staining in the contents of goblet cells of the crypts and in the mucus in the lumen of glands (FIG. 6A asterisk) supports the thought that SIMA135 is produced in a soluble form by colonic epithelial cells. In colon carcinoma specimens SIMA135 was extensively and heterogeneously expressed (FIG. 6B) with some focal accentuation in the mucus within malignant glands (arrow FIG. 6B). Some groups of invading cancer cells (FIG. 6C), were heavily stained showing the presence of SIMA135 on the basal, apical and lateral membranes as well as within the glandular mucus. There was a definite trend towards an association of intense staining with more malignant, invading glands as carcinoma cells deeper in the colonic serosa (FIG. 6C) and within draining blood vessels (FIG. 6D) were often strongly positive for the SIMA135 antigen. Control sections that were incubated with the secondary but not the primary antibody were free of staining.

EXAMPLE XVII

Figure 7:
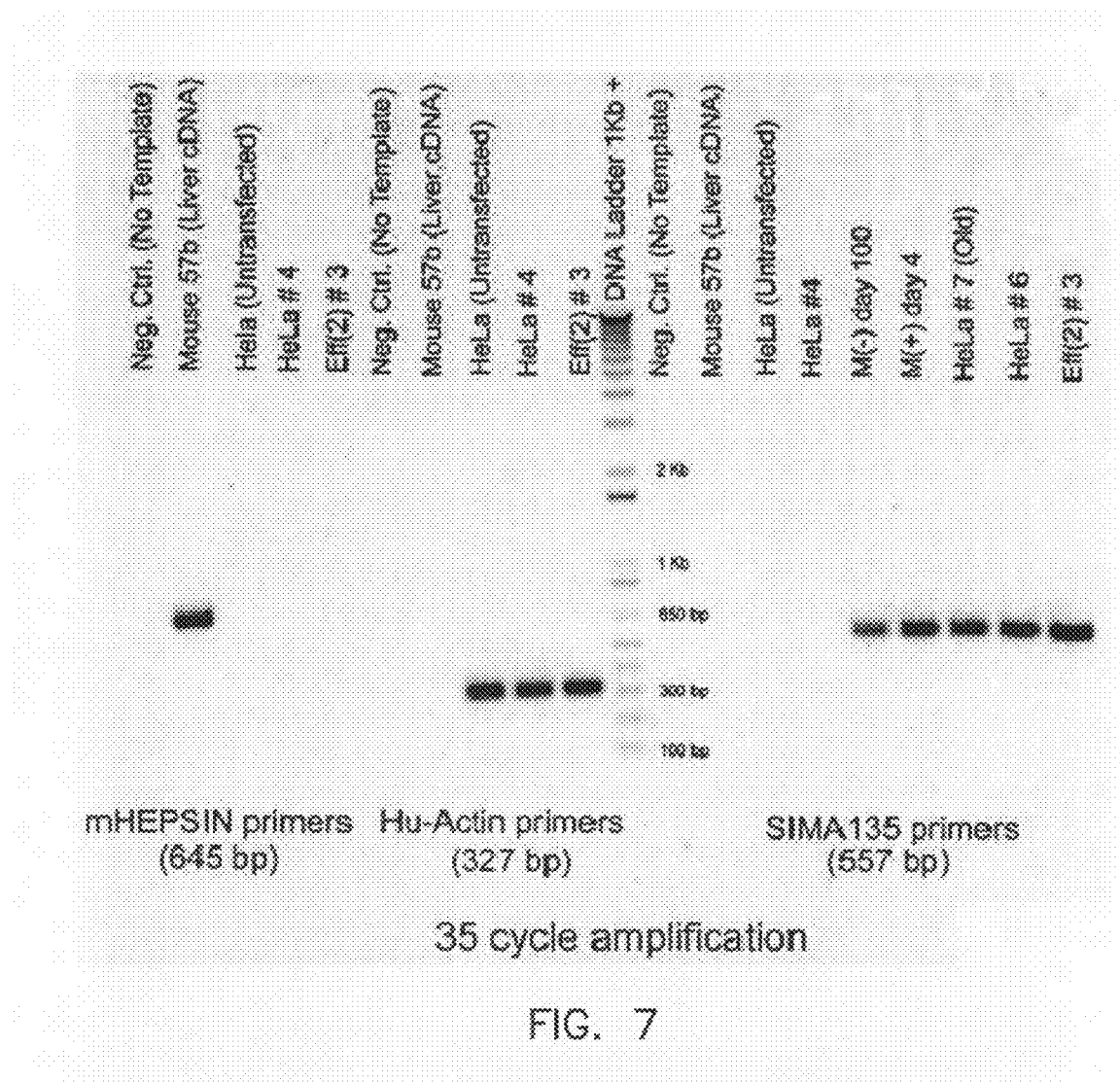
FIG. 7 is an RT-PCR analysis of 7 different cell lines used to examine expression of SIMA-135 mRNA.
Figure 8A:
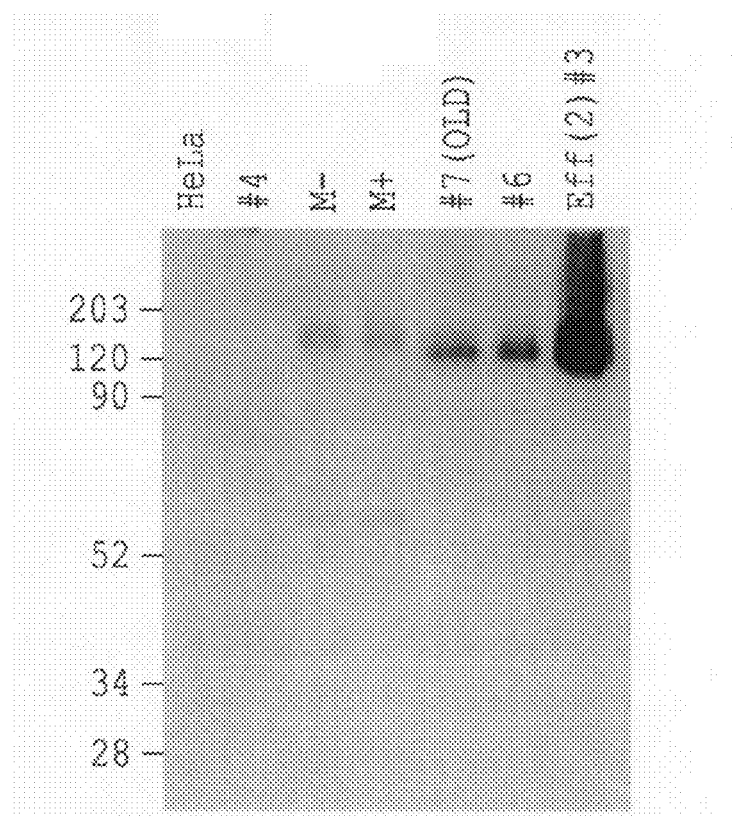
FIG. 8(A) is a 2-minute exposure of the blot.
Figure 8B:
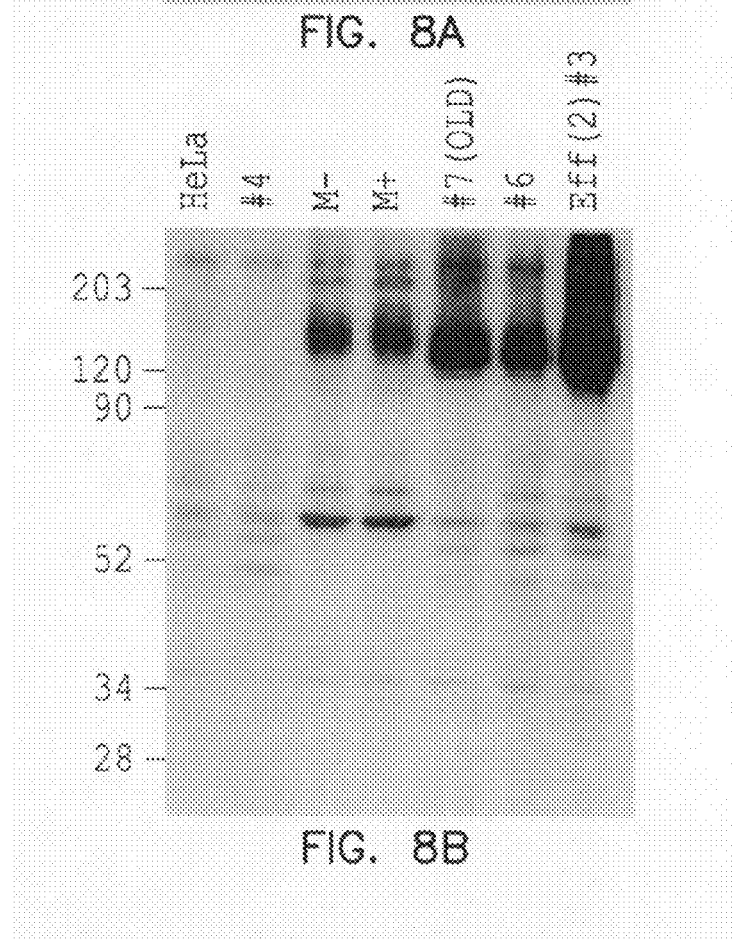
FIG. 8(B) is a 25-minute exposure of the same blot.

Following the transfection procedures described above for HeLa cells, 7 different cell lines were used to study and monitor expression of SIMA-135 mRNA. Of these cell lines, clone no. 3 produced a significant, appropriate base pair signal. The ability of these cell lines to transport in an in vitro study, to metastasize and to form tumors in SCID mice and to colonize secondary organs in SCIP mice was also studied. It was determined that clone 3 was able to detach and migrate through porous membranes and in vivo and to colonize secondary organs. These results demonstrate that SIMA135 is a key, central factor managing metastasis. The transformed clone no. 3 cells are also useful as the cellular system for identification of agents that promote or inhibit/minimize metastasis of malignant cells. Pursuant to the transfection procedures outlined above, 7 different cell lines were employed to study the effects of SIMA-135 expression. These cell lines are illustrated in FIG. 8. Following the analytic procedures for SIMA-135 RMA detection given above, these 7 cell lines were analyzed. FIG. 7 shows the results of the RT-PCR analysis of these 7 different cell lines monitoring SIMA-135 mRNA. Controls and irrelevant RT-PCR data is in the left-hand part of FIG. 1. The right-hand part of the figure shows a 600 bp amplified signal generated from SIMA-135 specific primers. The important lanes are HeLa (untransfected) which yields no signal, HeLa no. 4 which also yields no signal and Eff (2) no. 3 which is now called clone no. 3 and generates a substantial 600 bp signal. These data indicate that clone no. 3 cells have elevated levels of SIMA-135 mRNA.

Samples of these 7 cell lines were lysed and the cellular contents analyzed according to a standard Western blot procedure to determine the presence of SIMA-135 through binding with MoAb 41-2. FIG. 8 shows the Western blot on lysates prepared from the 7 different cell lines probed with MoAb 41-2. Two exposures of the blot are presented, 2 minutes and 25 minutes. The results demonstrate that clone no. 3 (Eff (2) no. 3) produces substantial levels of the SIMA-135 immunoreactive protein. This cloned cell line produces more SIMA-135 protein then even our highly metastatic HEp-3 cell line, M$^+$ also shown in the Figure. Clone #4 and parental HeLa cells produce no detectable SIMA-135 protein.

Once it was confirmed that SIMA-135 negative cells and SIMA-135 overexpressors had been obtained, these cells were tested for their malignant potential i.e. their ability to grow and form tumors in SCID mice and their ability to colonize secondary organs in SCID mice. Table I is a summary of two separate types of assays: Panel A shows the results of an experimental metastasis assay where the cells of interest are inoculated (i.v.) directly into the tail vein of the mice. A few weeks later, selected organs of the inoculated mice were analyzed for the presence of human cells (human DNA) in the background of total organ mouse DNA. The analysis was performed by real time PCR using human specific primers based on alu repeat sequences as described in the following reference (A. Zijlstra, et al., Cancer Research, 2002). The results shown in panel A indicate that clone no. 3 cells colonize and/or grow in mouse lung and bone marrow at levels substantially over that of similarly inoculated clone no. 4 cells. It is also apparent that clone no. 3 does not just spread all over the inoculated mice since another organ shown here, the pancreas, only contains near background levels of both clone no. 3 and clone no. 4 cells.

Panel B of Table 1 contains the results of a standard spontaneous metastasis assay where cells are inoculated subcutaneously in the flanks of SCID mice, tumors are allowed to develop to over 100 mg and then selected organs, usually the lungs, are analyzed for secondary metastatic deposits. The secondary metastases were measured by the same real time alu PCR procedures that are specific for human DNA. The results indicate that clone no. 3 and clone no. 4 form primary tumors of approximately equal size (weight in milligrams-mg). However, clone no. 3 appears to have metastasized to the lungs at a level that is at least 10 times greater than clone no. 4. It may be more than 10 times greater since the level of cells in the clone no. 4 lung is close to background (50-100 cells) at barely detectable levels.

The results demonstrate that the introduction or expression of the SIMA-135 protein into cells that normally do not produce it, conveys malignant properties to those cells. In order to characterize these two clones for properties that might indicate why they have gained malignant potential we carried out a few cell biological assays on the clones.

Figure 9:
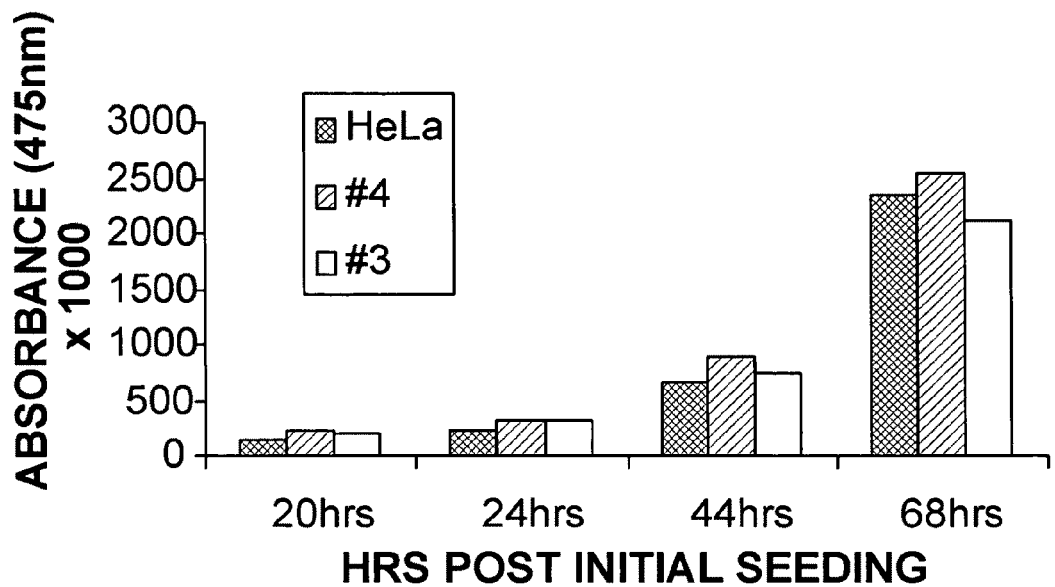
FIG. 9 is a bar graph showing the cell growth or proliferation of transfected cells in culture.

A cell growth or proliferation assay was carried out in cell culture according to the procedures given above. The results are shown in FIG. 9. The growth in vitro of these two clones is similar and also similar to the parental HeLa cells. Thus, simple proliferation rate is not the reason for their differential malignant potential.

Figure 10:
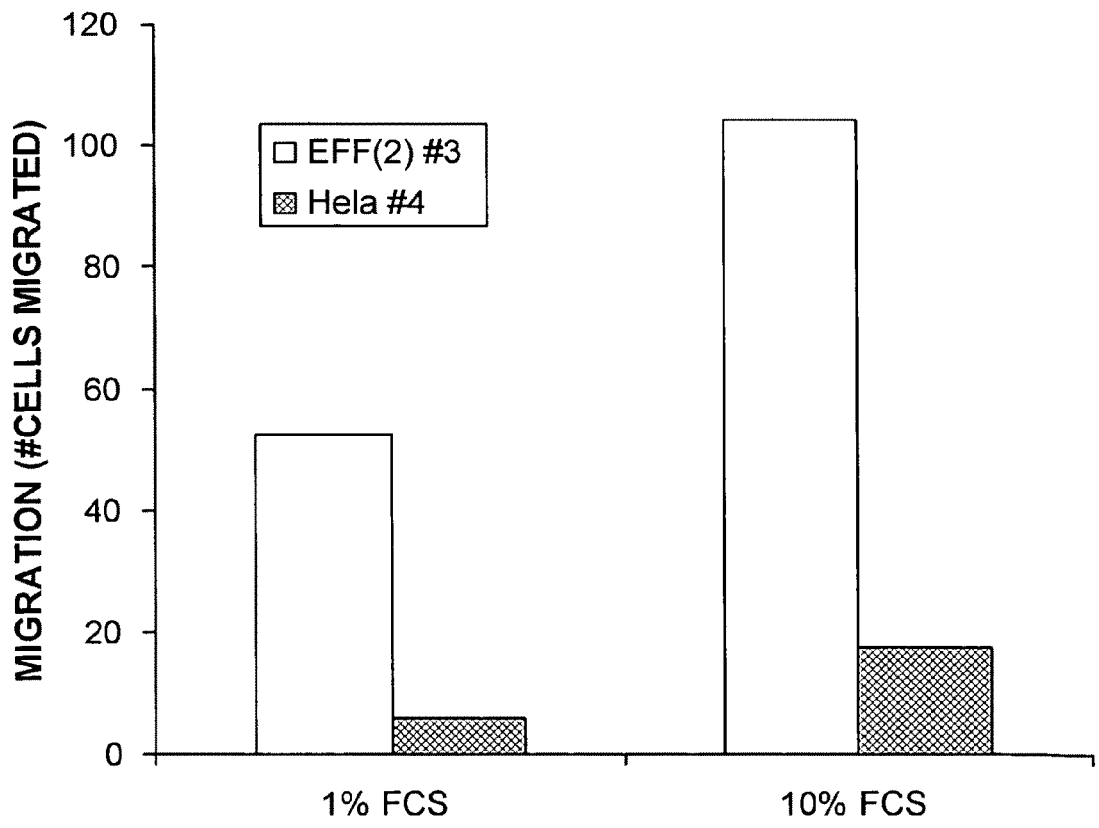
FIG. 10 is a bar graph showing the effectiveness of transwell migration through a porous filter membrane by transfected cells.

A trans-well migration assay whereby cells of interest are forced to migrate across a porous filter inserted between two chambers was also carried out. The assay was conducted with culture medium. The results are shown in FIG. 10. The upper chamber contains the cells in medium while the lower chamber contains enriched medium with fetal calf serum (FCS) to attract the migrating cells from the upper chamber. The results show that the clone no. 3 cells are much more migratory than clone #4 cells. This could be one of the acquired properties of SIMA-135 overexpressors that aid them in their malignant potential.

Preliminary data also indicate that clone no. 3 cells appear to be more resistant than clone no. 4 cells to apoptosis induced chemically by the compound ara C.

TABLE I

In Vivo malignancy of two HeLa clones; Clone #4 (SIMA-135 negative) and clone #3 (SIMA-135 overexpressors) inoculated into SCID mice.

A. Experimental Metastasis (i.v. inoculation into tail vein).

| | Calculated number of human cells/organ* | |
|---|---|---|
| | Clone #4 | Clone #3 |
| Lung | 150 | 2300 |
| Bone Marrow | <100 | 9,500 |
| Pancreas | 150 | 200 |

B. Spontaneous Metastasis (subcutaneous inoculation

| | Clone #4 inoculated mice | Clone #3 inoculated mice |
|---|---|---|
| Primary Tumor Weight (mg) | 227.5 +/− 68 (n = 8) | 184.1 +/− 26 (n = 7) |
| Human Cells in Lung (# cells)* | 250* | 2800* |

*based on real time alu PCR performed on total DNA extracted from organ excised 2 weeks after i.v. inoculation and 4 weeks after s.c. inoculation.

DOCUMENTS

Adham I M, Klemm U, Maier WM and Engel W. (1990). *Hum. Genet.*, 84, 125-8.

Bajorath J. (2000). *Proteins*, 39, 103-111.

Blom N, Gammeltoft S and Brunak S. (1999). *J. Mol. Biol.*, 294, 1351-1362.

Bork P and Beckmann G. (1993). *J. Mol. Biol.*, 231, 539-545.

Briner T J, Kuo M C, Keating K M, Rogers B L and Greenstein J L. (1993). *Proc. Natl. Acad. Sci. USA*, 90, 7608-7612.

Brooks P C, Lin J M, French D L and Quigley J P. (1993). *J. Cell Biol.*, 122, 1351-1359.

Chen CB and Wallis R. (2001). *J. Biol. Chem.*, 276, 25894-25902.

Falquet L, Pagni M, Bucher P, Hulo N, Sigrist C J, Hofmann K and Bairoch A. (2002). *Nucleic Acids Res.*, 30, 235-238.

Goebeler M, Kaufmann D, Brocker E B and Klein C E. (1996). *J. Cell Sci.*, 109 (Pt 7), 1957-1964.

Gorelik E, Galili U and Raz A. (2001). *Cancer Metastasis Rev.*, 20, 245-277.

Grogan M J, Pratt M R, Marcaurelle L A and Bertozzi C R. (2002). *Annu. Rev. Biochem.*, 71, 593-634.

Hanke J H, Gardner J P, Dow R L, Changelian P S, Brissette W H, Weringer E J, Pollok B A and Connelly P A. (1996). *J. Biol. Chem.*, 271, 695-701.

Hansen S G, Grosenbach D W and Hruby D E. (1999). Virology, 254, 124-137.

Hartmann E, Rapoport T A and Lodish H F. (1989). *Proc. Natl. Acad. Sci. USA*, 86, 5786-5790.

Hooper J D, Clements J A, Quigley J P and Antalis T M. (2001). *J. Biol. Chem.*, 276, 857-860.

King S W and Morrow K J, Jr. (1988). *Biotechniques*, 6, 856-861.

Martin G S. (2001). *Nat. Rev. Mol. Cell. Biol.*, 2, 467-475.

Maruo Y, Gochi A, Kaihara A, Shimamura H, Yamada T, Tanaka N and Orita K. (2002). *Int. J. Cancer*, 100, 486-490.

Matthew W D and Patterson P H. (1983). *Cold Spring Harb. Symp. Quant. Biol.*, 48 Pt 2, 625-631.

Mayer B J. (2001). *J. Cell Sci.*, 114, 1253-1263.

Nakai K and Kanehisa M. (1992). *Genomics*, 14, 897-911.

Nielsen-Preiss, S M and Quigley J P. (1993). *J Cell Biochem* 51:219-235

Ossowski L and Reich E. (1983). *Cell,* 33, 323-333.
Pawson T. (1995). *Nature,* 373, 573-580.
Resh M D. (1994) *Cell,* 76, 411-413.
Riggott M J and Matthew W D. (1996). *J. Neurosci. Methods,* 68, 235-245.
Rye P D and McGuckin M A. (2001). *Tumour. Biol.,* 22, 269-272.
Scherl-Mostageer M, Sommergruber W, Abseher R, Hauptmann R, Ambros P and Schweifer N. (2001). *Oncogene,* 20, 4402-4408.
Schultz J, Milpetz F, Bork P and Ponting C P. (1998). *Proc. Natl. Acad. Sci. USA,* 95, 5857-5864.
Sieron A L, Tretiakova A, Jameson B A, Segall M L, Lund-Katz S, Khan M T, Li S and Stocker W. (2000). *Biochemistry,* 39, 3231-3239.
Sleister H M and Rao A G. (2002). *J. Immunol. Methods,* 261, 213-220.
Songyang Z, Shoelson S E, Chaudhuri M, Gish G, Pawson T, Haser W G, King F, Roberts T, Ratnofsky S, Lechleider R J, Neel B G, Birge R B, Fajardo J E, Chou M M, Hanafusa H, Schaffhausen B and Cantley L C. (1993). *Cell,* 72, 767-778.
Soos G, Jones R F, Haas G P, Wang C Y. (1997). *Anticancer Res.,* 17, 4253-4258.
Stocker J W and Nossal G J. (1976). *Contemp. Top. Immunobiol.,* 5, 191-210.
Testa J E (1992). *Cancer Res.,* 52, 5597-5603.
Testa J E, Brooks P C, Lin J M and Quigley J P. (1999). *Cancer Res.,* 59, 3812-3820.
Wajih N, Walter J and Sane D C. (2002). *Circ. Res.,* 90, 46-52.
Williams C V, Stechmann C L and McLoon S C. (1992). Biotechniques, 12, 842-847.
Yammani R R, Seetharam S and Seetharam B. (2001). *J. Biol. Chem.,* 276, 44777-44784.
Zhang W, Trible R P and Samelson L E. (1998). *Immunity,* 9, 239-246.
U.S. Pat. No. 6,245,898.
A. Zijlstra, et al., Cancer Research, 2002.

All publications, patents and patent applications cited in the foregoing text are incorporated herein by reference.

While in the foregoing specification, this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated protein having SEQ ID NO: 1 that is glycosylated.

2. An isolated variant of SEQ ID NO: 1, wherein the variant results from the substitution of the glutamine with an arginine at amino acid 525.

3. An isolated variant of SEQ ID NO: 1, wherein the variant results from the substitution of the asparagine with a serine at amino acid 827.

* * * * *

UNITED STATES PATENT AND TRADEMARK OFFICE
CERTIFICATE OF CORRECTION

PATENT NO.      : 7,589,173 B2                          Page 1 of 1
APPLICATION NO. : 10/781564
DATED           : September 15, 2009
INVENTOR(S)     : Quigley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 291 days.

Signed and Sealed this

Twenty-first Day of September, 2010

David J. Kappos
*Director of the United States Patent and Trademark Office*

SEQUENCE LISTING

```
<160> NUMBER OF SEQ ID NOS: 10

<210> SEQ ID NO 1
<211> LENGTH: 836
<212> TYPE: PRT
<213> ORGANISM: Homo sapiens

<400> SEQUENCE: 1

Met Ala Gly Leu Asn Cys Gly Val Ser Ile Ala Leu Leu Gly Val Leu
1               5                  10                  15

Leu Leu Gly Ala Ala Arg Leu Pro Arg Gly Ala Glu Ala Phe Glu Ile
                20                  25                  30

Ala Leu Pro Arg Glu Ser Asn Ile Thr Val Leu Ile Lys Leu Gly Thr
            35                  40                  45

Pro Thr Leu Leu Ala Lys Pro Cys Tyr Ile Val Ile Ser Lys Arg His
        50                  55                  60

Ile Thr Met Leu Ser Ile Lys Ser Gly Glu Arg Ile Val Phe Thr Phe
65                  70                  75                  80

Ser Cys Gln Ser Pro Glu Asn His Phe Val Ile Glu Ile Gln Lys Asn
                85                  90                  95

Ile Asp Cys Met Ser Gly Pro Cys Pro Phe Gly Glu Val Gln Leu Gln
            100                 105                 110

Pro Ser Thr Ser Leu Leu Pro Thr Leu Asn Arg Thr Phe Ile Trp Asp
        115                 120                 125

Val Lys Ala His Lys Ser Ile Gly Leu Glu Leu Gln Phe Ser Ile Pro
    130                 135                 140

Arg Leu Arg Gln Ile Gly Pro Gly Glu Ser Cys Pro Asp Gly Val Thr
145                 150                 155                 160

His Ser Ile Ser Gly Arg Ile Asp Ala Thr Val Val Arg Ile Gly Thr
                165                 170                 175

Phe Cys Ser Asn Gly Thr Val Ser Arg Ile Lys Met Gln Glu Gly Val
            180                 185                 190
```

-continued

```
Lys Met Ala Leu His Leu Pro Trp Phe His Pro Arg Asn Val Ser Gly
        195                 200                 205

Phe Ser Ile Ala Asn Arg Ser Ser Ile Lys Arg Leu Cys Ile Ile Glu
210                 215                 220

Ser Val Phe Glu Gly Glu Gly Ser Ala Thr Leu Met Ser Ala Asn Tyr
225                 230                 235                 240

Pro Glu Gly Phe Pro Glu Asp Glu Leu Met Thr Trp Gln Phe Val Val
                245                 250                 255

Pro Ala His Leu Arg Ala Ser Val Ser Phe Leu Asn Phe Asn Leu Ser
            260                 265                 270

Asn Cys Glu Arg Lys Glu Glu Arg Val Glu Tyr Tyr Ile Pro Gly Ser
        275                 280                 285

Thr Thr Asn Pro Glu Val Phe Lys Leu Glu Asp Lys Gln Pro Gly Asn
    290                 295                 300

Met Ala Gly Asn Phe Asn Leu Ser Leu Gln Gly Cys Asp Gln Asp Ala
305                 310                 315                 320

Gln Ser Pro Gly Ile Leu Arg Leu Gln Phe Gln Val Leu Val Gln His
                325                 330                 335

Pro Gln Asn Glu Ser Asn Lys Ile Tyr Val Val Asp Leu Ser Asn Glu
            340                 345                 350

Arg Ala Met Ser Leu Thr Ile Glu Pro Arg Pro Val Lys Gln Ser Arg
        355                 360                 365

Lys Phe Val Pro Gly Cys Phe Val Cys Leu Glu Ser Arg Thr Cys Ser
    370                 375                 380

Ser Asn Leu Thr Leu Thr Ser Gly Ser Lys His Lys Ile Ser Phe Leu
385                 390                 395                 400

Cys Asp Asp Leu Thr Arg Leu Trp Met Asn Val Glu Lys Thr Ile Ser
                405                 410                 415

Cys Thr Asp His Arg Tyr Cys Gln Arg Lys Ser Tyr Ser Leu Gln Val
            420                 425                 430

Pro Ser Asp Ile Leu His Leu Pro Val Glu Leu His Asp Phe Ser Trp
        435                 440                 445

Lys Leu Leu Val Pro Lys Asp Arg Leu Ser Leu Val Leu Val Pro Ala
    450                 455                 460

Gln Lys Leu Gln Gln His Thr His Glu Lys Pro Cys Asn Thr Ser Phe
465                 470                 475                 480

Ser Tyr Leu Val Ala Ser Ala Ile Pro Ser Gln Asp Leu Tyr Phe Gly
                485                 490                 495

Ser Phe Cys Pro Gly Gly Ser Ile Lys Gln Ile Gln Val Lys Gln Asn
            500                 505                 510

Ile Ser Val Thr Leu Arg Thr Phe Ala Pro Ser Phe Gln Gln Glu Ala
        515                 520                 525

Ser Arg Gln Gly Leu Thr Val Ser Phe Ile Pro Tyr Phe Lys Glu Glu
    530                 535                 540

Gly Val Phe Thr Val Thr Pro Asp Thr Lys Ser Lys Val Tyr Leu Arg
545                 550                 555                 560

Thr Pro Asn Trp Asp Arg Gly Leu Pro Ser Leu Thr Ser Val Ser Trp
                565                 570                 575

Asn Ile Ser Val Pro Arg Asp Gln Val Ala Cys Leu Thr Phe Phe Lys
            580                 585                 590

Glu Arg Ser Gly Val Val Cys Gln Thr Gly Arg Ala Phe Met Ile Ile
        595                 600                 605

Gln Glu Gln Arg Thr Arg Ala Glu Glu Ile Phe Ser Leu Asp Glu Asp
```

-continued

```
              610                 615                 620
Val Leu Pro Lys Pro Ser Phe His His Ser Phe Trp Val Asn Ile
625                 630                 635                 640

Ser Asn Cys Ser Pro Thr Ser Gly Lys Gln Leu Asp Leu Leu Phe Ser
                645                 650                 655

Val Thr Leu Thr Pro Arg Thr Val Asp Leu Thr Val Ile Leu Ile Ala
                660                 665                 670

Ala Val Gly Gly Gly Val Leu Leu Leu Ser Ala Leu Gly Leu Ile Ile
                675                 680                 685

Cys Cys Val Lys Lys Lys Lys Lys Thr Asn Lys Gly Pro Ala Val
690                 695                 700

Gly Ile Tyr Asn Asp Asn Ile Asn Thr Glu Met Pro Arg Gln Pro Lys
705                 710                 715                 720

Lys Phe Gln Lys Gly Arg Lys Asp Asn Asp Ser His Val Tyr Ala Val
                725                 730                 735

Ile Glu Asp Thr Met Val Tyr Gly His Leu Leu Gln Asp Ser Ser Gly
                740                 745                 750

Ser Phe Leu Gln Pro Glu Val Asp Thr Tyr Arg Pro Phe Gln Gly Thr
                755                 760                 765

Met Gly Val Cys Pro Pro Ser Pro Pro Thr Ile Cys Ser Arg Ala Pro
770                 775                 780

Thr Ala Lys Leu Ala Thr Glu Glu Pro Pro Arg Ser Pro Glu
785                 790                 795                 800

Ser Glu Ser Glu Pro Tyr Thr Phe Ser His Pro Asn Asn Gly Asp Val
                805                 810                 815

Ser Ser Lys Asp Thr Asp Ile Pro Leu Leu Asn Thr Gln Glu Pro Met
                820                 825                 830

Glu Pro Ala Glu
        835

<210> SEQ ID NO 2
<211> LENGTH: 18
<212> TYPE: DNA
<213> ORGANISM: Homo sapiens

<400> SEQUENCE: 2
tccccaccgt cgttttcc                                                     18

<210> SEQ ID NO 3
<211> LENGTH: 21
<212> TYPE: DNA
<213> ORGANISM: Homo sapiens

<400> SEQUENCE: 3
ggttaggaac acggacgggt g                                                 21

<210> SEQ ID NO 4
<211> LENGTH: 19
<212> TYPE: PRT
<213> ORGANISM: Homo sapiens
<220> FEATURE:
<221> NAME/KEY: SITE
<222> LOCATION: 15
<223> OTHER INFORMATION: Xaa = Glycine  or Isoleucine
<220> FEATURE:
<221> NAME/KEY: SITE
<222> LOCATION: 17
<223> OTHER INFORMATION: Xaa = any amino acid

<400> SEQUENCE: 4
```

```
Phe Glu Ile Ala Leu Pro Arg Glu Ser Gln Ile Thr Val Leu Xaa Lys
 1               5                  10                  15

Xaa Gly Thr

<210> SEQ ID NO 5
<211> LENGTH: 19
<212> TYPE: PRT
<213> ORGANISM: Homo sapiens
<220> FEATURE:
<221> NAME/KEY: SITE
<222> LOCATION: 17
<223> OTHER INFORMATION: Xaa = any amino acid

<400> SEQUENCE: 5

Phe Glu Ile Ala Leu Pro Arg Glu Ser Asn Ile Thr Val Leu Ile Lys
 1               5                  10                  15

Xaa Gly Thr

<210> SEQ ID NO 6
<211> LENGTH: 13
<212> TYPE: PRT
<213> ORGANISM: Homo sapiens
<220> FEATURE:
<221> NAME/KEY: SITE
<222> LOCATION: (1)...(4)
<223> OTHER INFORMATION: Xaa = any amino acid

<400> SEQUENCE: 6

Xaa Xaa Xaa Xaa Ile Pro Gly Ser Thr Thr Asn Pro Glu
 1               5                  10

<210> SEQ ID NO 7
<211> LENGTH: 13
<212> TYPE: PRT
<213> ORGANISM: Homo sapiens

<400> SEQUENCE: 7

Val Glu Tyr Tyr Ile Pro Gly Ser Thr Thr Asn Pro Glu
 1               5                  10

<210> SEQ ID NO 8
<211> LENGTH: 12
<212> TYPE: PRT
<213> ORGANISM: Homo sapiens
<220> FEATURE:
<221> NAME/KEY: SITE
<222> LOCATION: 1, 3
<223> OTHER INFORMATION: Xaa = any amino acid

<400> SEQUENCE: 8

Xaa Tyr Xaa Leu Gln Val Pro Ser Asp Ile Leu His
 1               5                  10

<210> SEQ ID NO 9
<211> LENGTH: 12
<212> TYPE: PRT
<213> ORGANISM: Homo sapiens

<400> SEQUENCE: 9

Ser Tyr Ser Leu Gln Val Pro Ser Asp Ile Leu His
 1               5                  10

<210> SEQ ID NO 10
<211> LENGTH: 8
<212> TYPE: PRT
```

-continued

```
<213> ORGANISM: Artificial Sequence
<220> FEATURE:
<223> OTHER INFORMATION: A synthetic FLAG epitope

<400> SEQUENCE: 10

Asp Tyr Lys Asp Asp Asp Asp Lys
 1               5
```